US011786755B2

(12) United States Patent
Ohishi

(10) Patent No.: US 11,786,755 B2
(45) Date of Patent: Oct. 17, 2023

(54) RADIOTHERAPY SUPPORT APPARATUS, RADIOTHERAPY SYSTEM, AND RADIOTHERAPY SUPPORT METHOD

(71) Applicant: Canon Medical Systems Corporation, Otawara (JP)

(72) Inventor: Satoru Ohishi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 733 days.

(21) Appl. No.: 16/784,536

(22) Filed: Feb. 7, 2020

(65) Prior Publication Data

US 2020/0254279 A1 Aug. 13, 2020

(30) Foreign Application Priority Data

Feb. 7, 2019 (JP) ................................. 2019-020486
Feb. 5, 2020 (JP) ................................. 2020-018100

(51) Int. Cl.
| | | |
|---|---|---|
| A61B 5/00 | (2006.01) | |
| A61N 5/10 | (2006.01) | |
| G16H 20/40 | (2018.01) | |
| A61B 5/026 | (2006.01) | |
| A61B 6/03 | (2006.01) | |
| A61B 6/00 | (2006.01) | |
| A61B 8/06 | (2006.01) | |

(52) U.S. Cl.
CPC ............ *A61N 5/1039* (2013.01); *G16H 20/40* (2018.01); *A61B 5/0263* (2013.01); *A61B 6/032* (2013.01); *A61B 6/037* (2013.01); *A61B 6/507* (2013.01); *A61B 8/06* (2013.01); *A61N 2005/1074* (2013.01); *A61N 2005/1087* (2013.01)

(58) Field of Classification Search
CPC ....... A61B 5/026; A61B 5/0263; A61B 5/055; A61B 6/032; A61B 6/037; A61B 6/04; A61B 6/507; A61B 8/06; A61B 8/0833; A61B 8/0891; A61B 8/4245; A61N 2005/1052; A61N 2005/1055; A61N 2005/1061; A61N 2005/1074; A61N 2005/1087; A61N 5/1038; A61N 5/1039; G16H 20/40; G16H 30/40; G16H 50/50
See application file for complete search history.

(56) References Cited

U.S. PATENT DOCUMENTS

| | | | |
|---|---|---|---|
| 2010/0228116 A1* | 9/2010 | Lu | ........................ A61N 5/103 703/11 |
| 2014/0121495 A1 | 5/2014 | Dempsey | |
| 2015/0133714 A1 | 5/2015 | Inaniwa et al. | |

FOREIGN PATENT DOCUMENTS

| | | |
|---|---|---|
| JP | 2013-233233 A | 11/2013 |
| JP | 2015-533581 A | 11/2015 |
| JP | 2017-176056 A | 10/2017 |

* cited by examiner

*Primary Examiner* — Mark D Remaly
(74) *Attorney, Agent, or Firm* — Oblon, McClelland, Maier & Neustadt, L.L.P.

(57) ABSTRACT

According to one embodiment, a radiotherapy support apparatus has processing circuitry. The processing circuitry obtains an activity level distribution representing radiation resistance in a tumor area of a subject, and produces a first treatment plan in which a radiation administered dose to the tumor area changes within the tumor area in accordance with the activity level distribution.

22 Claims, 12 Drawing Sheets

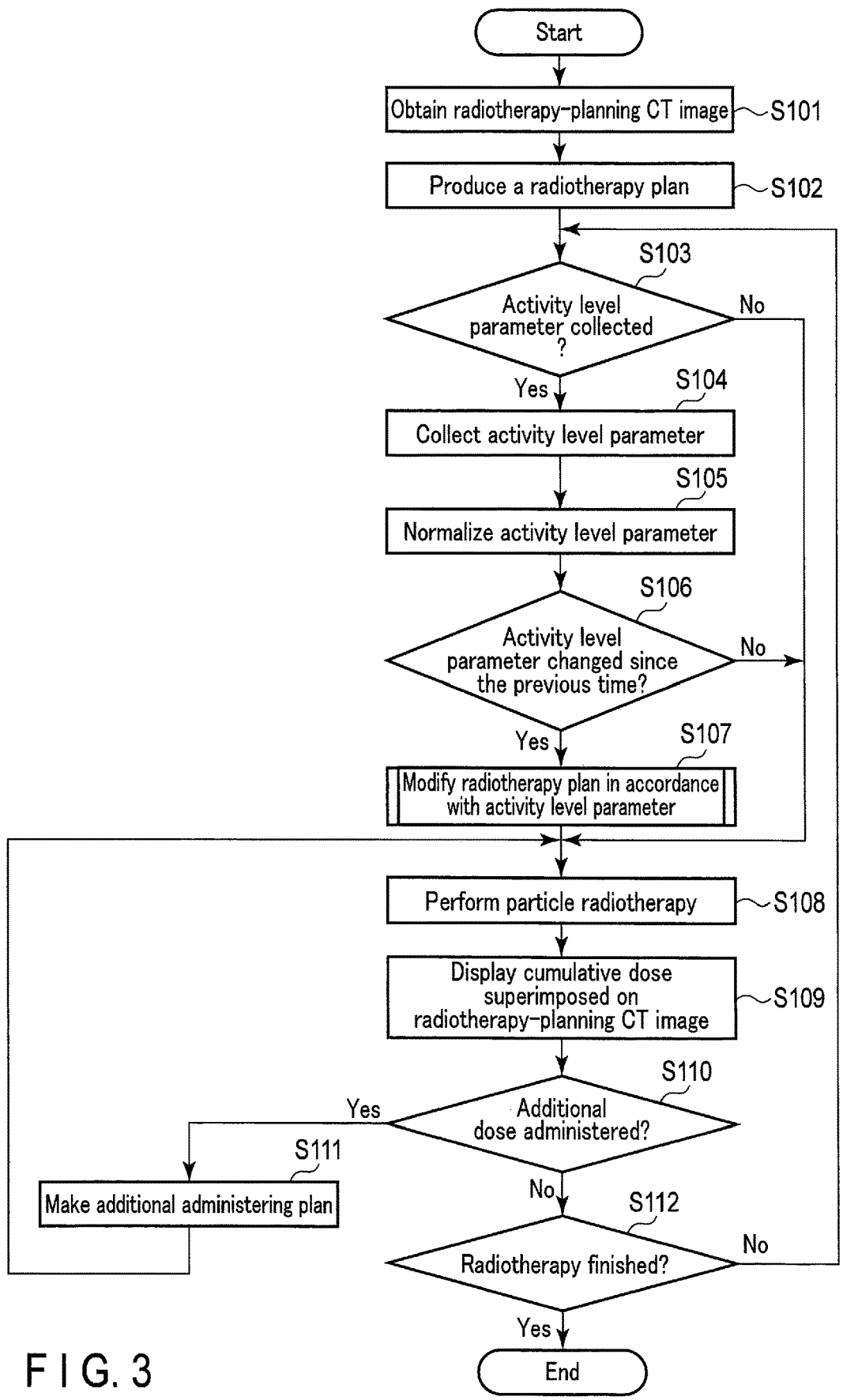
F I G. 3

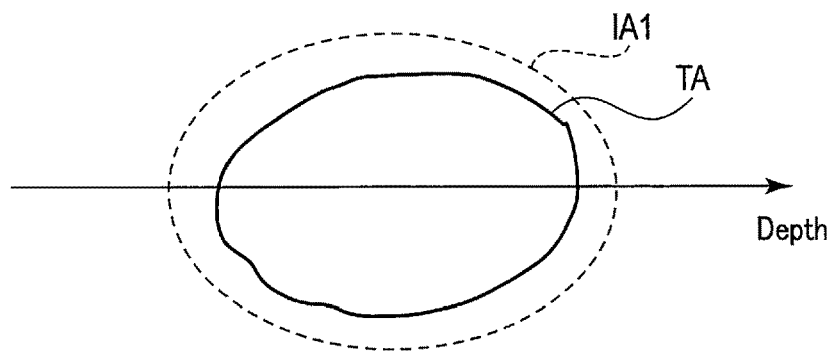
F I G. 4A
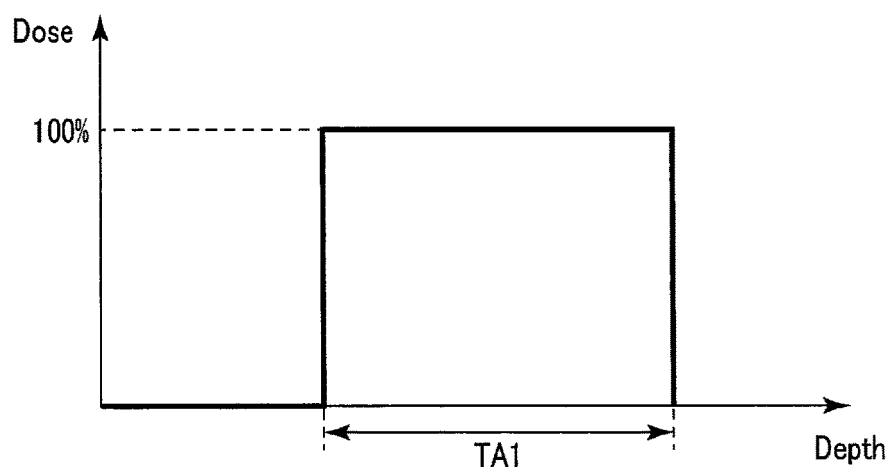
F I G. 4B
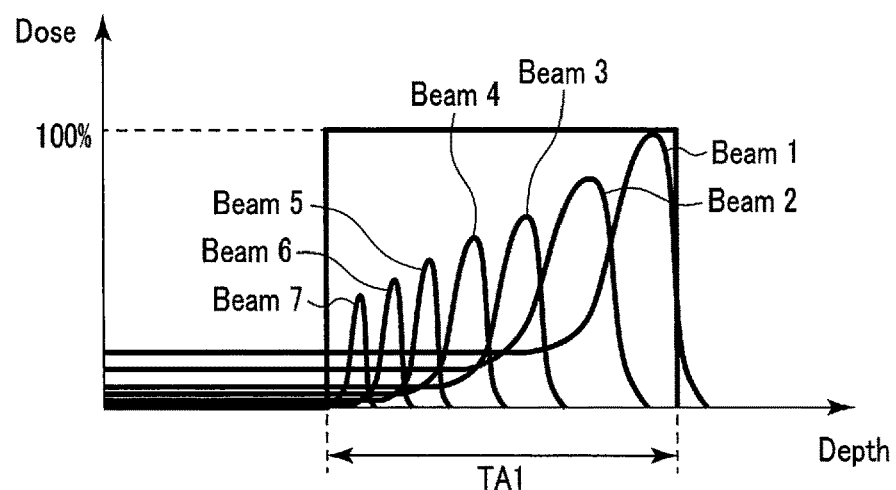
F I G. 4C

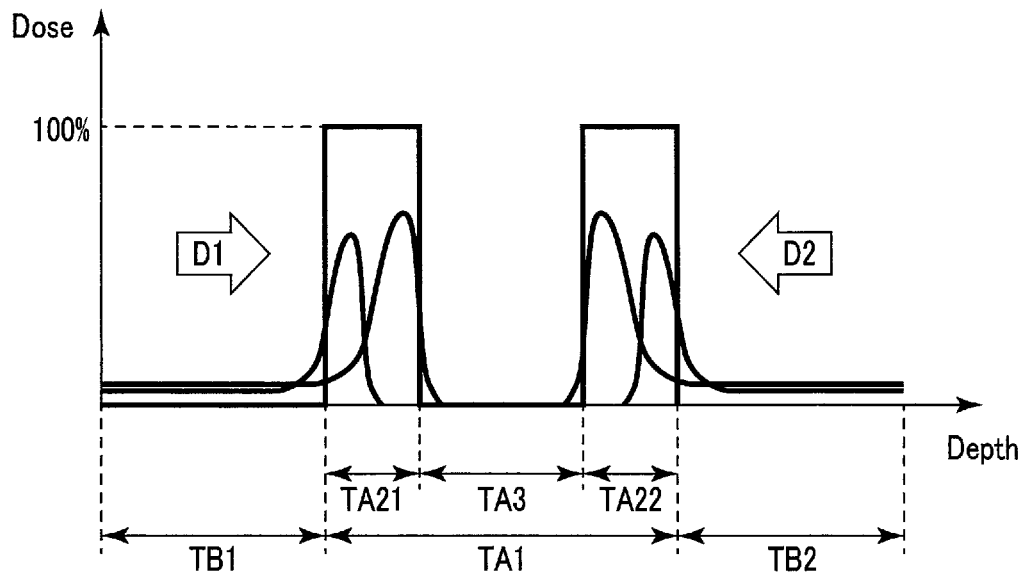
F I G. 7F
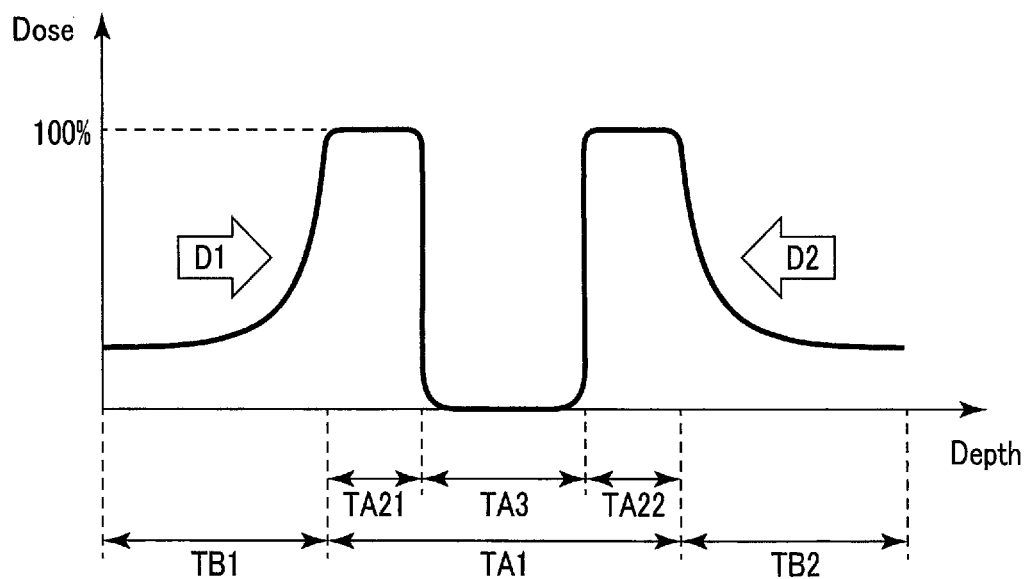
F I G. 7G

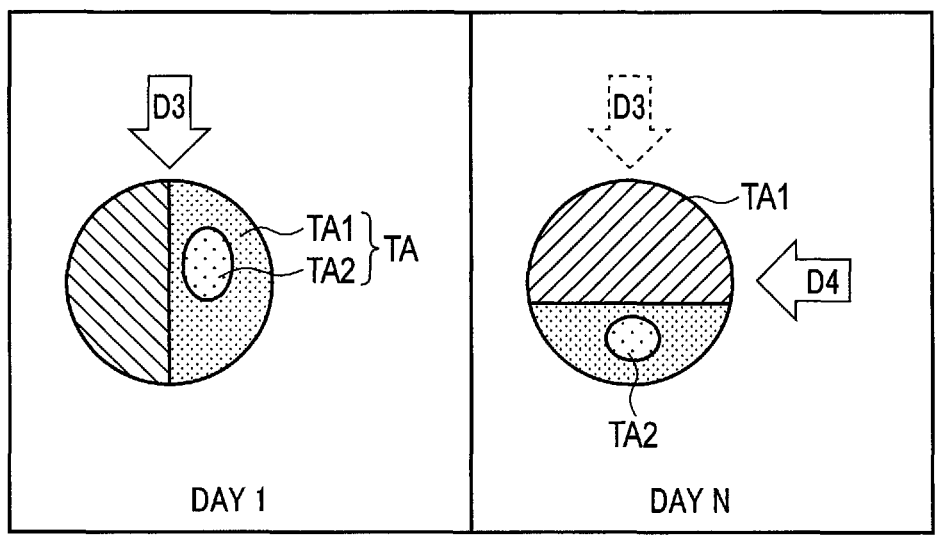
F I G. 11

RADIOTHERAPY SUPPORT APPARATUS, RADIOTHERAPY SYSTEM, AND RADIOTHERAPY SUPPORT METHOD

CROSS-REFERENCE TO RELATED APPLICATIONS

This application is based upon and claims the benefit of priority from the Japanese Patent Application No. 2019-020486, filed Feb. 7, 2019, and the Japanese Patent Application No. 2020-018100, filed Feb. 5, 2020, the entire contents of all of which are incorporated herein by reference.

FIELD

Embodiments described herein relate generally to a radiotherapy support apparatus, a radiotherapy system, and a radiotherapy support method.

BACKGROUND

Studies have been conducted on the subject of radiotherapy with the use of particle beams such as heavy-ion beams and proton rays. Examples of heavy particles are carbon ions, silicon ions, and argon ions. A feature of the particle therapy is to concentrate a radiation dose at a tumor area due to the Bragg peak. It is possible to form a spread-out Bragg peak (SOBP) by applying particle beams in the same irradiation direction while changing the Bragg peak depth of each particle beam along a single depth direction. If the width of the SOBP becomes large, however, a dose to tissue located in the front of a tumor approaches to a dose to a tumor area.

On the other hand, a Bragg peak cannot be formed in X-ray radiotherapy, and it is difficult to concentrate a radiation dose at a tumor area only from a single direction. For this reason, techniques such as intensity modulated radio therapy (IMRT) and volumetric modulated arc therapy (VMAT) have become more popular in recent years. The IMRT is a method of irradiating a patient from multiple directions with X-rays in an optimized dose form. The VMAT is a technique for improving dose concentration on a tumor area through rotation of a gantry while changing a rotation rate and a dose rate, and simultaneously irradiating a patient with intensity-modulated X-rays.

However, regardless of the adoption of such advanced techniques, tumor recurrences will occur. A hypoxia state of tumor tissue is cited as one of the reasons for this. The inside of the tumor area contains hypoxic cells that cannot acquire sufficient amounts of blood flow. At the same time, it is known that a radiotherapy has a weaker effect on cancer tissue in a hypoxia state within a tumor area.

BRIEF DESCRIPTION OF THE DRAWINGS

FIG. 3 has a flowchart showing an example of a flow of a radiotherapy performed in accordance with an activity level parameter in the radiotherapy system shown in FIG. 1.

FIG. 4A is a drawing showing an example of a planning target volume according to an original radiotherapy plan produced by a radiotherapy planning apparatus shown in FIG. 1.

FIG. 4B is an example of an expected administered dose distribution in a depth direction indicated by an arrow shown in FIG. 4A.

FIG. 4C is an example of a plurality of particle beams that constitute an expected administered dose distribution according to a radiotherapy plan shown in FIG. 4B.

FIG. 7F is a drawing in which an expected administered dose distribution and a plurality of radiation beams are superimposed in an irradiation direction D1 and an irradiation direction D2 shown in FIG. 7E.

FIG. 7G is an example of spread-out Bragg peaks formed by the plurality of radiation beams shown in FIG. 7F.

FIG. 11 is a diagram showing an example of a modification of a therapy plan relating to an X-ray therapy.

DETAILED DESCRIPTION

Figure 1:
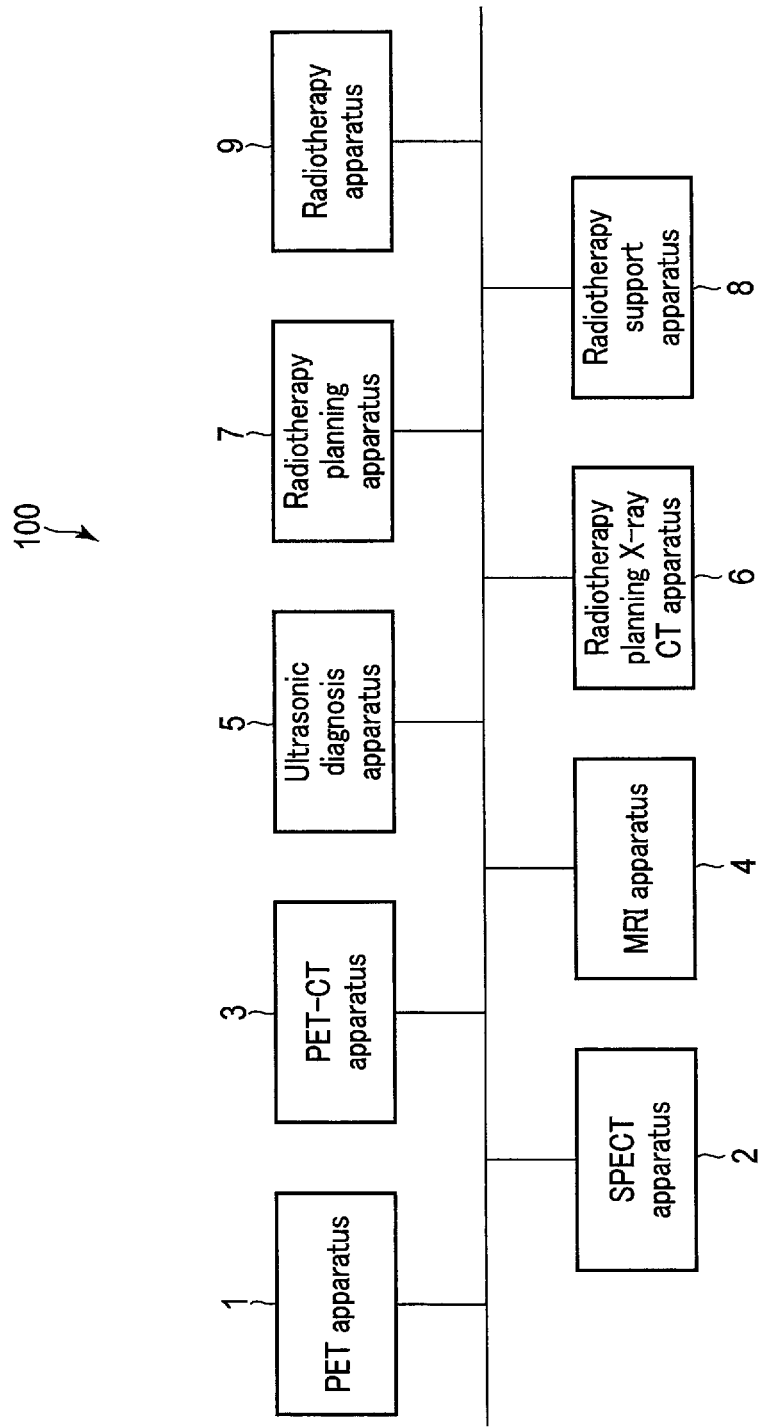
FIG. 1 is a diagram showing a configuration example of a radiotherapy system according to a first embodiment.

In general, according to one embodiment, a radiotherapy support apparatus has processing circuitry. The processing circuitry obtains an activity level distribution representing radiation resistance in a tumor area of a subject, and produces a first treatment plan in which a radiation administered dose to the tumor area changes within the tumor area in accordance with the activity level distribution.

The radiotherapy support apparatus, the radiotherapy system, and the radiotherapy support method according to this embodiment will be described below with reference to the accompanying drawings. In the descriptions hereinafter, constituent elements having the same or almost the same functions will be denoted by the same reference symbols, and a duplicate description will be made only when required. Where the same element is illustrated in different drawings, the dimensions and scales may be different between the drawings.

The radiotherapy support apparatus, the radiotherapy system, and the radiotherapy support method according to the present embodiment are used for radiotherapy using radiation, such as X-rays and particle beams. Suppose the radiotherapy support apparatus, the radiotherapy system, and the radiotherapy support method are, if radiotherapy using particle beams is provided, a particle therapy support apparatus, a particle therapy system, and a particle therapy support. Herein, "particle beams" is a general term for proton rays and heavy particles.

In general, radiosensitivity of a cell varies depending on a type of the cell and its cell-division cycle, conditions of cell-surrounding environment (such as a pH value, a temperature, and an amount of oxygen), a radiation quality, and a dose rate, etc. Herein, radiation resistance of a cell is defined as a level of sensitivity of a cell to radiation. In other words, if the radiosensitivity of a cell is high, the radiation resistance of a cell is low, and the cell is susceptible to a radiation dose; if the radiosensitivity of a cell is low, the radiation resistance of a cell is high, and the cell is less susceptible to a radiation dose. The radiosensitivity is affected by an activity level of a cell. In other words, if the activity level is high, the radiosensitivity is high, and if the activity level is low, the radiosensitivity is low.

It is said that such temporal changes in the radiation resistance are caused by three factors, which will be described below. The first factor causes a change over a short period of time; the second factor causes a change over an intermediate period of time; and the third factor causes a change over a long period of time.

When a cell divides, a period between one division and the next is called a "cell-division cycle". The cell-division cycle consists of the following phases: a DNA synthesis phase during which DNA (deoxyribonucleic acid) is replicated ("S phase"); a mitosis phase during which a cell divides into two cells ("M phase"); a G1 phase between mitosis and the S phase; a G2 phase between the S phase and the M phase; and a resting phase during which a cell has stopped its division and a cell has left the cycle ("G0 phase"). In such a cell-division cycle, it is said that the activity level of a cell becomes high during the M phase and low during the S phase and the G0 phase. Thus, the radiation resistance of a tumor area varies with time, in accordance with a cell-division cycle, for example. This causes a temporal change in a radiation resistance over a short period of time.

On the other hand, cancer cells acquire oxygen and nutrients from nutrition vessels; however, when the cancer grows, the oxygen and nutrients from the nutrition vessels are no longer sufficient, and some of the cancer cells are not supplied with sufficient amount of oxygen and nutrients. Under such a circumstance, the cancer cells first lower their own activity levels so as to survive, and simultaneously cause angiogenesis so as to supply themselves with sufficient amounts of oxygen and nutrients. Such a low-activity level state leads to a hypoxia state, under which it is known that radiation resistance is low. Once sufficient amounts of oxygen and nutrients can be acquired, the cancer cells increase their activity levels. At this time, some cancer cells are now unable to acquire sufficient amounts of oxygen and nutrients, whereas others are supplied with sufficient amounts of oxygen and nutrients. Those cancer cells lower their activity levels, and simultaneously cause angiogenesis, so as to supply themselves with sufficient amounts of oxygen and nutrients. Thus, such dynamic changes in the activity levels of the cancer cells cause a change in radiation resistance. It is known that this change in radiation resistance occurs over a period of time a little longer than the aforementioned short period of time.

Furthermore, suppose a radiation therapy, for example, causes a lethal effect upon tumor cells having low radiation resistance. In this case, blood flows will no longer be stolen from the tumor cells in a hypoxia state, the environment of the tumor cells that have been in an under-nourished state and a hypoxia state will greatly improve due to improvement of blood flows, and these tumor cells will thus be reactivated. It is known that this change in radiation resistance occurs over a period of time longer than that during which the change is caused by the above-described second factor.

Accordingly, in the present embodiment, radiotherapy support apparatus that modifies a radiotherapy plan produced by a radiotherapy planning apparatus in accordance with a parameter relating to radiation resistance of a tumor area will be described as an example, on the assumption that the radiation resistance in the tumor area changes with time in accordance with a cell cycle and surroundings. In the descriptions hereinafter, the parameter relating to radiation resistance of the tumor area will be referred to as an "activity level parameter".

FIG. 1 is a diagram showing a configuration example of a radiotherapy system 100 including the radiotherapy support apparatus 8 and the radiotherapy apparatus 9 according to the present embodiment. As shown in FIG. 1, the radiotherapy system 100 includes a PET (positron emission tomography) apparatus 1, a SPECT (single photon emission CT) apparatus 2, a PET-CT apparatus 3 (an integrated type capable of PET and computed tomography), an MRI (magnetic resonance imaging) apparatus 4, an ultrasonic diagnosis apparatus 5, a radiotherapy-planning X-ray CT apparatus 6, a radiotherapy planning apparatus 7, a radiotherapy support apparatus 8, and a radiotherapy apparatus 9, which are connected to each other via a network.

The PET apparatus 1, the SPECT apparatus 2, the PET-CT apparatus 3, the MRI apparatus 4, the ultrasonic diagnosis apparatus 5, and the radiotherapy-planning X-ray CT apparatus 6 are medical modalities that generate three-dimensional medical images of a patient.

The PET apparatus 1 counts a pair of 511 keV gamma rays generated upon pair annihilation of each of the positrons generated from radionuclides accumulated in a patient and a corresponding one of electrons existing around the radionuclides through use of coincidence circuitry, thereby generating a three-dimensional PET image expressing the spatial distribution of the radionuclides based on coincidence count signals from the coincidence circuitry.

The SPECT apparatus 2 detects single photon gamma rays generated from radionuclides accumulated in an object by using a radiation detector to generate a three dimensional SPECT image expressing the spatial distribution of the radionuclides based on the detection signals from the radiation detector.

The PET-CT apparatus 3 is a medical modality in which a PET apparatus and a CT apparatus are integrated. For example, the PET-CT apparatus 3 generates a PET image and a CT image, and generates a superimposed image (fusion image) of the PET image and the CT image. In the PET-CT apparatus 3, the PET image is used as data for functional information, for example. The CT image is used as data for profile information and attenuation correction, for example.

The MRI apparatus 4 applies, for example, RF pulses from an RF coil to excite target atomic nuclei existing in the patient placed in a static magnetic field, and acquires MR signals generated from the target atomic nuclei using the RF coil. The MRI apparatus 4 then generates a three dimensional MR image expressing the spatial distribution of the target atomic nuclei based on the MR signals from the RF coil.

The ultrasonic diagnosis apparatus 5 generates an ultrasonic image in which a tomographic image of a living body soft tissue is expressed through use of an ultrasonic pulse reflection method.

The radiotherapy-planning X-ray CT apparatus 6 applies X-rays to a patient from an X-ray tube while rotating a rotating frame that holds the X-ray tube and an X-ray detector at high speed, and detects the X-rays passed through the patient using the X-ray detector. The radiotherapy-planning X-ray CT apparatus 6 then generates a three-dimensional therapy-planning CT image (therapy-planning medical image) expressing the spatial distribution of the X-ray attenuation coefficients of substances on the X-ray transmission path, based on projection data from the X-ray detector. The radiotherapy-planning X-ray CT apparatus 6 obtains a therapy-planning CT image, while a patient is being secured to a bed, etc. by a fixing tool. The fixing tool may be a tool for partially securing the patient through covering their body part, like a mask, or may be a tool stationarily fixed to a bed that has a shape adapted to a body (shape) of a patient and capable of securing the patient when the patient lies on the bed. The top plate of the radiotherapy-planning X-ray CT apparatus 6 has a flat shape akin to the top plate of the radiotherapy apparatus 9, so that a patient's body posture does not change between the time of CT imaging and the time of radiotherapy. When imaging to obtain a therapy-planning CT image is performed, a tube voltage of a predetermined condition is set.

The radiotherapy system 100 has a radiotherapy-planning X-ray CT apparatus 6 but the present embodiment is not limited to this example. In other words, the radiotherapy system 100 may have a medical image diagnosis apparatus, such as a cone beam CT apparatus, an MRI apparatus, or a nuclear medicine diagnostic apparatus, etc. as a supplementary apparatus, instead of the radiotherapy-planning X-ray CT apparatus 6, as long as it can generate a three-dimensional medical image data (therapy-planning medical image data) for patient therapy planning. However, to make the following descriptions specific, suppose that the radiotherapy system 100 has the radiotherapy-planning X-ray CT apparatus 6 as a medical image diagnosis apparatus that can generate three-dimensional medical image data (therapy-planning medical image data) for patient's therapy planning.

The radiotherapy planning apparatus 7 is a computer which produces a radiotherapy plan for the patient by using a three-dimensional medical image. The radiotherapy plan information is supplied to the radiotherapy support apparatus 8. The radiotherapy planning apparatus 7 converts a CT value into an electron density or a physical density based on the CT image obtained by the radiotherapy-planning X-ray CT apparatus 6. The radiotherapy planning apparatus 7 generates a radiotherapy plan so as to realize a target internal dose distribution based on distribution of the electron density or the physical density.

The radiotherapy support apparatus 8 also serves as an information system that manages schedule information of radiotherapy, and radiotherapy plan information, medical images, etc. As such an information system, for example, an OIS (oncology information system) is known. The radiotherapy support apparatus 8 supplies radiotherapy plan information to the radiotherapy apparatus 9, for example.

The radiotherapy apparatus 9 is an apparatus that treats a patient by irradiating a target tumor, etc. in the patient with particle beams in accordance with a radiotherapy plan. The radiotherapy apparatus 9 includes a particle therapy apparatus such as a proton therapy apparatus and a heavy particle therapy apparatus. In the particle therapy, the majority of the energy of particle beams irradiated on a patient is released at a certain depth within the patient's body in accordance with the energy. In other words, the particle beam has a peak (Bragg peak) at a specific depth depending on its energy. The depth indicates a distance from a body surface along the beam axis of the particle beam. Furthermore, the planning target volume including a tumor area, etc. in the patient's body has a thickness in the depth direction. For this reason, in a particle therapy, due to different levels of energy, a plurality of particle beams form a range of an absorbed dose having an approximately uniform width (that is, spread-out Bragg peak; SOBP) in the depth direction in accordance with the thickness. The radiotherapy apparatus 9 has an accelerator (not shown) that accelerates electron beams, a target with which electrons collide so as to generate X-rays, a rotation gantry (not shown) for irradiating a patient with the generated X-rays from a desired angle, and a patient locator apparatus (not shown) used for locating the patient who lies thereon. In the case where the radiotherapy apparatus 9 is a particle treatment apparatus, it has an accelerator that accelerates particles, a beam line (not shown) that guides the particles accelerated by the accelerator, a rotational gantry (not shown) that irradiates a patient with particle beams from a desired angle, and a patient locator apparatus (not shown) used for determining a location of the patient who lies thereon. As a particle beam irradiation method, scanning capable of realizing a complicated dose distribution is suitable.

The SOBP may be formed by a ridge filter, or may be formed through layering the particle beams through changing the energy of the particle beams. To change the energy of the particle beams, a method of emitting a particle beam of a desired energy through controlling an acceleration speed with an accelerator, and a method of emitting a particle beam with constant energy from an accelerator and changing the energy of the particle beam with an energy attenuator, are known. The former method is possible when the accelerator is a synchrotron, and the latter method is mainly adopted in a case where the accelerator is a synchrotron or a synch cyclotron. A hybrid method of generating a particle beam of a discrete energy with a synchrotron, and minutely adjusting the energy with an attenuator, is also possible.

The radiotherapy system 100 may further include an X-ray angio apparatus or a picture archiving and communication system (PACS), etc. On the other hand, an activity level parameter may be obtained externally to the radiotherapy system 100. In other words, the radiotherapy system 100 does not necessarily include the PET apparatus 1, the SPECT apparatus 2, the PET-CT apparatus 3, the MRI apparatus 4, and the ultrasonic diagnosis apparatus 5. Similarly, the radiotherapy apparatus 9 may be provided externally to the radiotherapy system 100. In other words, the radiotherapy system 100 according to the present embodiment may be a system for producing and modifying a radiotherapy plan.

Figure 2:
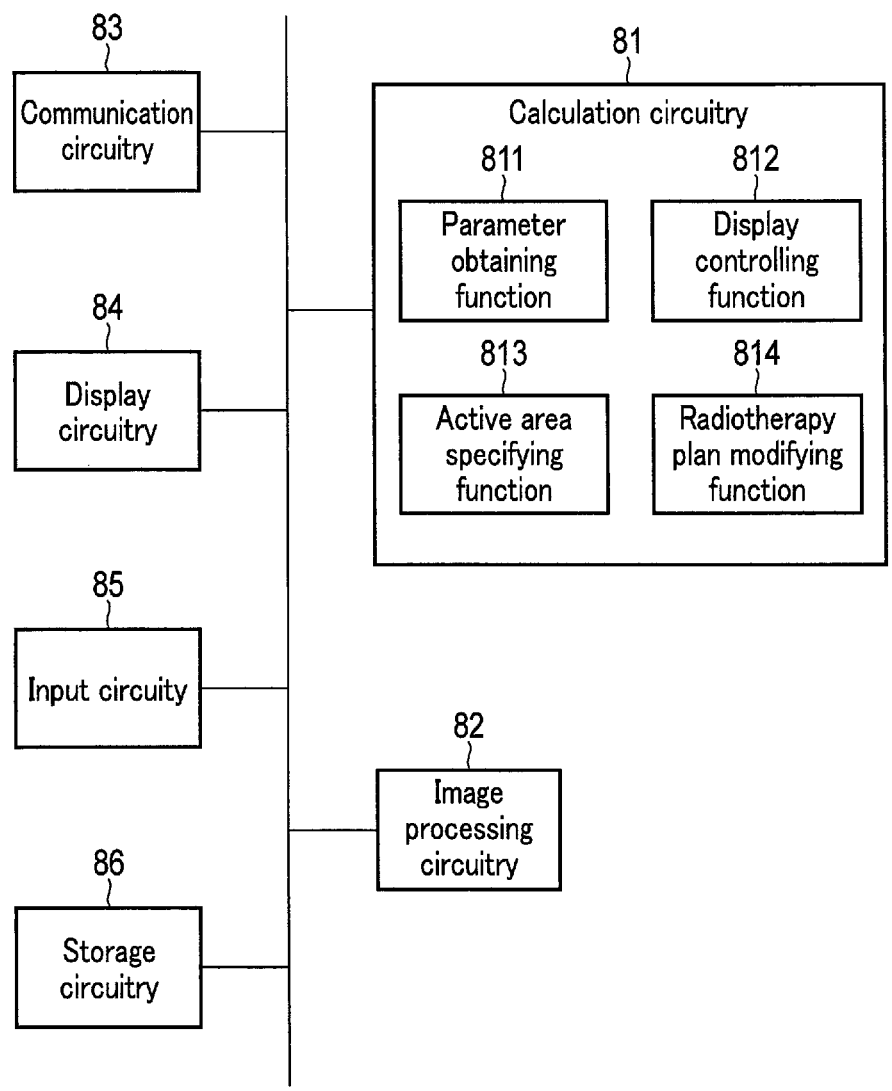
FIG. 2 is a diagram showing a configuration example of a radiotherapy support apparatus shown in FIG. 1.

FIG. 2 is a diagram showing a configuration example of the radiotherapy support apparatus 8 shown in FIG. 1. As shown in FIG. 2, the radiotherapy support apparatus 8 is a computer that supports radiotherapy by the radiotherapy apparatus 9. As shown in FIG. 2, the radiotherapy support apparatus 8 includes processing circuitry 81, image processing circuitry 82, communication circuitry 83, display circuitry 84, input circuitry 85, and storage circuitry 86. The processing circuitry 81, the image processing circuitry 82, the communication circuitry 83, the display circuitry 84, the input circuitry 85, and the storage circuitry 86 are communicably connected to each other via a bus.

The processing circuitry 81 controls the entire operation of the radiotherapy support apparatus 8. The processing circuitry 81 executes a program related to radiotherapy support (referred to as "a radiotherapy support program" hereinafter), and supports a radiotherapy performed by the radiotherapy apparatus 9 in accordance with radiation resistance of a tumor area. The processing circuitry 81 includes, as hardware resources, a processor such as a CPU (central processing unit), MPU (micro processing unit), or GPU (graphics processing unit) and memories such as a ROM (read only memory) and a RAM (random access memory).

The processing circuitry 81 according to the present embodiment performs, through the radiotherapy support program, a parameter obtaining function 811, a display controlling function 812, an active area specifying function 813, and a radiotherapy plan modifying function 814.

In the parameter obtaining function 811, the processing circuitry 81 obtains an activity level parameter. The activity level parameter includes, for example, at least one of perfusion information or metabolism information in a tumor area. In the parameter obtaining function 811, the processing circuitry 81 obtains an activity level parameter from, for example, a medical modality of the radiotherapy system 100. In other words, the processing circuitry 81 obtains an activity level distribution representing radiation resistance of the tumor area. As mentioned above, the activity level distribution in the tumor area changes with time, in accordance with a cell-division cycle of tumor cells in the tumor area and surroundings, etc. For this reason, in the parameter obtaining function 811, the processing circuitry 81 re-obtains an activity level parameter at predetermined timing. The predetermined timing may be provided every time a therapy is carried out, or every other multiple several therapy sessions, for example, every other three days. The predetermined timing at which an activity level parameter is re-obtained is set in advance, and is stored in the storage circuitry 86, for example.

For example, the processing circuitry 81 in the parameter obtaining function 811 obtains, as the activity level parameter, the measured perfusion information or metabolism information from the PET apparatus 1, the SPECT apparatus 2, the PET-CT apparatus 3, the MRI apparatus 4, the ultrasonic diagnosis apparatus 5, or the radiotherapy-planning X-ray CT apparatus 6. For example, in the parameter obtaining function 811, the processing circuitry 81 obtains, as the activity level parameter, the measured metabolism information from the PET apparatus 1, the SPECT apparatus 2, or the PET-CT apparatus 3. If the measured metabolism information does not have quantitative properties, the processing circuitry 81 in the parameter obtaining function 811 normalizes the obtained activity level parameter.

The predetermined timing for re-obtaining the activity level parameter is not limited to timing based on the number of times a therapy is carried out or the number of days passed, and may rather be determined in accordance with factors that cause a change in the activity level, such as a cell-division cycle. The predetermined timing for re-obtaining the activity level parameter may be determined in accordance with a change in a measurement value related to the activity level parameter. For example, the activity level parameter may be measured every time a therapy is carried out, and a value and a distribution of the activity level parameter may be monitored; and in accordance with an amount of change in the activity level parameter or a size of change in the area, a decision on whether or not to re-obtain the measured value as the activity level parameter may be taken.

The activity level parameter may be measured by a medical modality provided externally to the radiotherapy system 100. For example, the processing circuitry 81 in the parameter obtaining function 811 obtains, as an activity level parameter, the perfusion information measured by an X-ray CT apparatus, which is an external device of the radiotherapy system 100. Alternatively, the processing circuitry 81 in the parameter obtaining function 811 may calculate the activity level parameter in accordance with a distance from a micro blood vessel imaged by a high-definition X-ray CT apparatus.

The activity level parameter is not limited to the value measured by any type of medical modality, and may be an estimated value. The processing circuitry 81 in the parameter obtaining function 811 predicts an activity level parameter. This prediction can be made based on a previously measured value, a cell-division cycle, and the number of days passed since the last measurement, for example. When the activity level parameter is treated as a relative value, the prediction may be made based on a cell-division cycle and the number of days passed since the last measurement, for example.

In the display controlling function 812, the processing circuitry 81 controls the operation of the display circuitry 84. The processing circuitry 81 in the display controlling function 812 generates image data the display circuitry 84 is caused to display. The image data includes, for example, therapy-planning CT image data (therapy-planning medical image data) on which an activity level parameter, a classification regarding the radiosensitivity in the tumor area, or a cumulative value of an amount of administered particle beams (a dose) regarding each area of the tumor area is superimposed. The image data includes image data for displaying an operation screen, for example.

The processing circuitry 81 in the active area specifying function 813 specifies, based on the activity level distribution, a plurality of areas classified by the radiation resistance of the tumor area. Specifically, the processing circuitry 81 specifies an active area where the radiation resistance is relatively low and a non-active area where the radiation resistance is relatively high, based on the activity level distribution. The active area is an area where the sensitivity to radiation is high in the tumor area. The specification of the active area is based on the obtained activity level parameter. The specification of the active area is performed at timing after the activity level parameter is obtained, for example.

In the radiotherapy plan modifying function 814, the processing circuitry 81 modifies the radiotherapy plan in accordance with the activity level distribution.

Specifically, the processing circuitry 81 modifies the radiotherapy plan in accordance with the activity level parameter. When the radiotherapy plan is modified, the processing circuitry 81 in the radiotherapy plan modifying function 814 determines a planning target volume into which radiations are irradiated in accordance with the distribution of the specified active area. The processing circuitry 81 in the radiotherapy plan modifying function 814 determines an expected administered dose distribution in accordance with the determined planning target volume. The processing circuitry 81 in the radiotherapy plan modifying function 814 determines an expected administered dose distribution by performing a simulation of radiation dose based on the expected administered dose distribution. As described above, the activity level distribution in the tumor area changes with time. For this reason, the processing circuitry 81 in the radiotherapy plan modifying function 814 modifies the radiotherapy plan each time the activity level parameter is obtained or the active area is specified, for example.

The processing circuitry 81 may be realized by an ASIC (application specific integrated circuit), or an FPGA (field programmable gate array). The processing circuitry 81 may be realized by another type of CPLD (complex programmable logic device) or SPLD (simple programmable logic device).

Each of the functions 811 through 814 is not necessarily implemented by a single processing circuit. Processing circuitry may be configured by combining a plurality of independent processors, and the processors may execute respective programs to implement the functions 811 through 814.

The image processing circuitry 82 includes, as hardware resources, a processor such as a CPU, a GPU, a MPU and memories such as a ROM and a RAM. The image processing circuitry 82 applies various types of image processing to three dimensional medical images. For example, the image processing circuitry 82 generates two dimensional medical images for display by applying three dimensional medical image processing such as volume rendering, surface rendering, image value projection processing, MPR (Multi-Planar Reconstruction) processing, and CPR (Curved MPR) processing to three dimensional medical images. Note that the image processing circuitry 82 may be implemented by an ASIC, FPGA, CPLD, or SPLD which can implement the above image processing.

The communication circuitry 83, via wires (not shown) or wirelessly, performs a data communication with the PET apparatus 1, the SPECT apparatus 2, the PET-CT apparatus 3, the MRI apparatus 4, the ultrasonic diagnosis apparatus 5, the radiotherapy-planning X-ray CT apparatus 6, the radiotherapy planning apparatus 7, and the radiotherapy apparatus 9, which constitute the radiotherapy system 100.

The display circuitry 84 displays various types of display information. The display circuitry 84 outputs, for example, a medical image (CT image) generated by the processing circuitry 81 in which the display controlling function 812 is implemented, and a graphical user interface (GUI) or the like for receiving, and various types of operations from the operator. As the display circuitry 84, one, or two or more displays of discretionary types can be used as appropriate. For example, as the display circuitry 84, a CRT (cathode ray tube) display, a liquid crystal display (LCD), an organic electro luminescence display (OELD), a light emitting diode (LED) display, or a plasma display can be used as appropriate. The display circuitry 84 is arranged on a wall of an operation room (not shown), for example.

The display circuitry 84 may be arranged at any location in the operation room. The display circuitry 84 may be provided at any location in a treatment room (not shown). The display circuitry 84 may be of a desktop type, or may be comprised of a tablet device, etc. capable of wireless communication. As the display circuitry 84, one, or two or more projectors may be used.

The input circuitry 85 accepts various types of instructions from a person involved in radiotherapy, such as radiological technologist or a doctor. As the input circuitry 85, a keyboard, a mouse, various types of switches, and the like may be used. The input circuitry 85 supplies an output signal corresponding to the received instruction to the processing circuitry 81 via a bus.

The storage circuitry 86 is a storage such as an HDD (hard disk drive), an SSD (solid state drive), or integrated circuit storage which stores various types of information. Alternatively, the storage circuitry 86 may be a drive assembly or the like which reads and writes various types of information from and to portable storage media such as a CD (compact disc)-ROM drive, a DVD (digital versatile disc) drive, or flash memory. The storage area of the storage circuitry 86 may be in an external storage device connected via a network. For example, the storage circuitry 86 stores the radiotherapy plan supplied from the radiotherapy planning apparatus 7, the therapy-planning CT image, a dose distribution (radiation strength distribution), and the activity level parameter measured by each modality, etc.

Herein, the operation of each part involved in the modification of the radiotherapy plan will be described in detail with reference to the drawings. FIG. 3 has a flowchart showing an example of a flow of the radiotherapy performed in accordance with the activity level parameter in the radiotherapy system 100 shown in FIG. 1.

In step S101, the radiotherapy-planning X-ray CT apparatus 6 obtains a therapy-planning CT image of the tumor area and the vicinity thereof. The imaging to obtain a therapy-planning CT image is performed when the patient is secured to a bed, etc. by a fixing tool and a condition of a predetermined tube voltage is set. The obtained therapy-planning CT image is transferred to the radiotherapy planning apparatus 7.

In step S102, the radiotherapy planning apparatus 7 produces a radiotherapy plan. To produce a radiotherapy plan, a spatial dose distribution is generated from information regarding the patient, a time distribution of the dose is considered, and an optimum therapy device, an optimum irradiation method, and optimum irradiation conditions, etc. are then determined.

First, the radiotherapy planning apparatus 7 converts a CT value of the therapy-planning CT image into electron density data or physical density data. This conversion requires a conversion table of pre-obtained CT values, and or electron density data or physical density data, for example. The conversion table is stored in, for example, a storage circuitry, etc. in the radiotherapy planning apparatus 7. Thereafter, the radiotherapy planning apparatus 7 produces a radiotherapy plan based on the electron density data or the physical density distribution. The processing regarding the producing of the radiotherapy plan includes pre-processing and planning processing.

In the pre-processing, the radiotherapy planning apparatus 7 identifies a gross tumor volume in the therapy-planning CT image. The radiotherapy planning apparatus 7 determines area planning target volume based on the identified tumor area, allowing for a margin determined in consideration of body motion of the patient and uncertainty, etc. of the therapy device. Herein, a particle treatment apparatus is used as the radiotherapy apparatus 9 will be first described. FIG. 4A is a drawing showing an example of the planning target volume IA1 based on an original particle therapy plan produced by the particle therapy planning apparatus 7. In the example shown in FIG. 4A, the gross tumor volume is the area surrounded by the solid line, and the planning target volume IA1 according to the original plan is the area surrounded by the broken line. In the case of the presence of an organ with a high risk of suffering from side effects caused by radiation exposure in the vicinity of the planning target volume IA1 according to the original plan, the particle therapy planning apparatus 7 identifies the organ as an at-risk organ. Thereafter, the particle therapy planning apparatus 7 determines an expected dose to the planning target volume IA1 according to the original plan, and an exposure limit for the at-risk organ, etc. FIG. 4B is an example of an expected administered dose distribution in a depth direction indicated by an arrow shown in FIG. 4A. It can also be said that FIG. 4B is an example of an expected administered dose distribution according to the particle therapy plan. The particle therapy planning apparatus 7 determines an expected administered dose distribution so that the planning target volume IA1 is irradiated with a predetermined dose of particle beams, for example. In the example shown in FIG. 4B, suppose that a 100% dose is an expected administered dose distribution allocated on a time basis, per therapy.

Figure 4D:
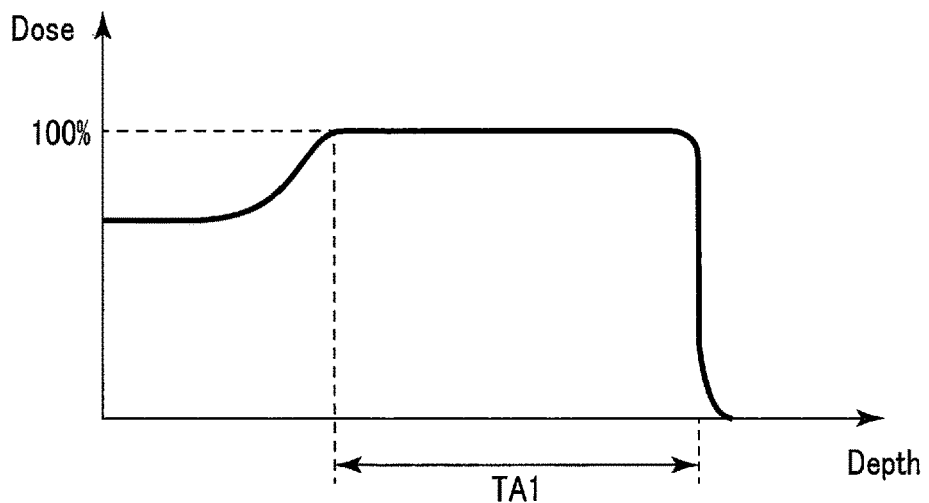
FIG. 4D is an example of a spread-out Bragg peak formed by the plurality of particle beams shown in FIG. 4C.

In the planning processing, the particle therapy planning apparatus 7 produces a particle therapy plan. The particle therapy plan includes a simulation of particle beam. The simulation of particle beam is performed based on the expected administered dose distribution shown in FIG. 4B. The particle beam has an ionization peak called a Bragg peak at a depth of a certain purpose. The depth of the Bragg peak of the particle beam is changed in accordance with the change of energy of the particle beam. Under such a circumstance, in order to irradiate the irradiation area uniformly, it is possible to form a spread-out Bragg peak (SOBP) that is spread out in accordance with a size and a depth of the irradiation area, through the use of a plurality of particle beams having different energy. In other words, the simulation regarding the particle beam can be expressed as a determination of the number of applied particle beams to realize the expected administered dose distribution and the energy of the applied particle beams. FIG. 4C is an example of a plurality of particle beams that realize an administered dose distribution expected by the particle therapy plan shown in FIG. 4B. FIG. 4D is an example of the spread-out Bragg peak formed by the plurality of particle beams shown in FIG. 4C.

The particle therapy plan may be generated by forward planning or inverse planning. When the particle therapy plan is produced by forward planning, a planner determines the irradiation conditions, such as an irradiation direction and a particle beam irradiation strength, etc. for each irradiation direction. The particle therapy planning apparatus 7 calculates a radiation dose distribution based on the determined irradiation direction and particle beam irradiation strength, etc. for each irradiation direction. The planner modifies the parameters, such as the irradiation direction and the particle beam irradiation strength, etc. for the particle therapy planning apparatus 7, based on the obtained radiation dose distribution. The particle therapy planning apparatus 7 once again calculates a radiation dose distribution based on the changed irradiation direction and particle beam irradiation strength, etc. The particle therapy planning apparatus 7 repeats the above processing until a desired radiation dose distribution is obtained, so that irradiation conditions are determined and a particle therapy plan is produced. On the other hand, when the particle therapy plan is produced by inverse planning, the particle therapy planning apparatus 7 obtains irradiation conditions, such as a dose to the planning target volume, a dose limit to the at-risk organ, and a dose limit to normal tissue other than the at-risk organ. Changing various parameters, the particle therapy planning apparatus 7 repeats the simulation until a particle therapy plan that satisfies the obtained irradiation conditions is produced.

Thereafter, the obtained particle therapy plan, the radiation dose distribution, and a dose volume histogram (DVH), etc. are checked by the planner and a doctor. The DVH is made from the particle therapy plan and the radiation dose distribution, for example. When it is determined that there are no problems as a result of the checking, the obtained particle therapy plan, etc. is authorized and transferred to the particle therapy support apparatus 8. The storage circuitry 86 of the particle therapy support apparatus 8 stores the particle therapy plan produced in the above-described manner and the therapy-planning CT image, etc.

In step S103, the processing circuitry 81 that enables the radiotherapy plan modifying function 814 determines whether or not to collect the activity level parameter. This determination is made based on an output of the input circuitry 85 in accordance with user input, for example. Thereafter, if it is determined that the activity level parameter should be collected, the processing proceeds to step S104 (collection of activity level parameter); if it is not so determined, the processing proceeds to step S108.

This determination may be performed at a predetermined cycle. The predetermined cycle may be every two days, every three days, or every week. This determination may be made based on a cumulative value of the dose, an amount of change in the size of the tumor area, and whether or not the amount of change in the shape of the tumor area exceeds a predetermined threshold. The threshold value, etc. used for the determination should be preset and stored in the storage circuitry 86, etc. If the cycle or timing of the modification of the particle therapy plan is predetermined, the determination is not necessarily made.

In step S104, the activity level parameter is collected. The irradiation of particle beam to the tumor area serving as the therapy target is performed several times. The typical number of times the irradiation is performed is 30. In the first therapy session, since there are no past activity level parameters, collection of an activity level parameter is recommended. The activity level parameter includes, for example, at least one of perfusion information or metabolism information in the tumor area. The measured perfusion information or metabolism information is related to the activity of the tumor area.

The perfusion information in the tumor area is measured by a perfusion test using the PET apparatus 1, for example. The perfusion information in the tumor area may be measured by a blood flow scintigraphy test using the SPECT apparatus 2, or by a perfusion test using the PET-CT apparatus 3, the MRI apparatus 4, or the ultrasonic diagnosis apparatus 5. The perfusion test may be performed using the radiotherapy-planning X-ray CT apparatus 6. Alternatively, the perfusion information may be estimated in accordance with a distance from a micro blood vessel imaged by a high-definition X-ray CT apparatus.

The metabolism information in the tumor area may be measured by oxygen metabolism imaging using the PET apparatus 1, for example. The metabolism information in the tumor area may be measured by sugar metabolism imaging using the PET apparatus 1 (for example, an FDG-PET test). The metabolism information in the tumor area may be measured by fatty acid imaging using the SPECT apparatus 2, or by oxygen metabolism imaging or sugar metabolism imaging using the PET-CT apparatus 3. Other than the above, the metabolism imaging using other pharmaceutical preparations, such as amino acid, may be adopted.

The measured activity level parameter is transferred to the particle therapy support apparatus 8. The processing circuitry 81 that enables the parameter obtaining function 811 obtains the activity level parameter obtained in the above-described manner. The obtained activity level parameter includes, for example, the image data such as the PET image data, the CT image data, the ultrasonic image data, or the MRI image data, or the image data obtained through analysis of such image data. For example, when the perfusion information of the brain is obtained by an X-ray CT apparatus, the activity level parameter includes a cerebral blood flow (CBF), a cerebral blood volume (CBV), and a map of a mean transit time (MTT) or a time-to-peak (TTP).

The activity level parameter is not limited to the measured perfusion information or metabolism information. For example, the processing circuitry 81 that enables the parameter obtaining function 811 may estimate the activity level parameter through predicting a cell-division cycle or angiogenesis based on the activity level parameters measured in the past. As described above, the cell-division cycle or angiogenesis is correlative to the radiosensitivity cycle of cells. The activity level parameters measured in the past may be those measured for the same patient or for a different patient.

In step S105, the processing circuitry 81 that enables the parameter obtaining function 811 normalizes the obtained activity level parameter. In general, the value measured in the perfusion test using the MRI apparatus 4 or the ultrasonic diagnosis apparatus 5, for example, is not a quantitative value. Although it is said that the value measured in the perfusion test using an X-ray CT apparatus is a quantitative value, the measured value described herein is not the perfusion information of a cell. For this reason, there is a case where this measured value cannot be treated as a quantitative value of perfusion information of a cell in the tumor area. In view of the above matters, the processing circuitry 81 that enables the parameter obtaining function 811 further obtains an activity level parameter (perfusion information and/or metabolism information) of a normal body part in the vicinity of the tumor area. The processing circuitry 81 that enables the parameter obtaining function 811 normalizes the activity level parameter of the tumor area with the use of the activity level parameter of the normal body part. Thus, the processing circuitry 81 that enables the parameter obtaining function 811 calculates the activity level parameter of the tumor area as a value relative to the activity level parameter of the normal body part. When it is possible to regard the measured activity level parameter of the tumor area as a quantitative value, this step may be skipped.

Thereafter, in step S106, the processing circuitry 81 that enables the radiotherapy plan modifying function 814 compares those activity level parameters. The activity level parameters to be compared are the activity level parameter newly collected in step S104, and the activity level parameter collected in the past or the temporal planning target volume in the therapy plan. In a first therapy session, since there is no activity level parameters obtained in the past, the newly-collected activity level parameter is compared with the planning target volume included in the therapy plan. If the activity level in the planning target volume is approximately constant and there is no area where the activity level is low, the processing proceeds to step S108. If there is an area where the activity level is low, the processing proceeds to step S107. On the other hand, if the collection of the activity level parameter is done second time or thereafter, the newly-collected activity level parameter is compared with the previously-collected activity level parameter. If there is no change to a certain extent in the planning target volume as a result of the comparison of those activity level parameters, the processing proceeds to step S108. If there is a change to a certain extent in the planning target volume, the processing proceeds to step S107. If there is an area, besides the tumor area, where the activity level is higher than a certain level, there is a possibility that the tumor has metastasized; accordingly, a warning message is displayed to this effect. The various types of thresholds used to determine whether or not the activity level parameter has been modified since the last therapy, such as a threshold of the activity level and a threshold of an amount of change in the activity level, are preset and stored in the storage circuitry 86, for example.

Figure 5:
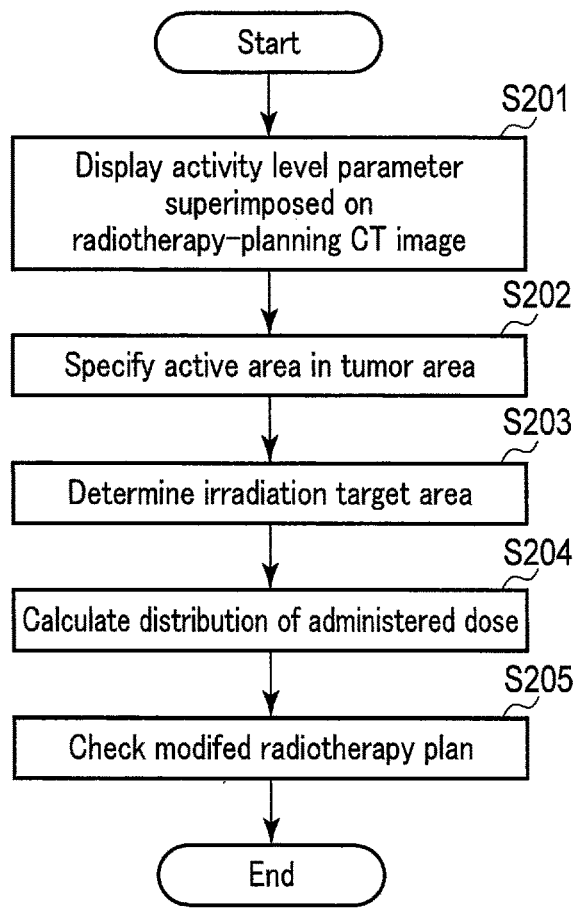
FIG. 5 is a flowchart showing an example of a flow of modification of a radiotherapy plan in accordance with an activity level parameter in the radiotherapy shown in FIG. 3.

In step S107, the particle therapy plan is modified in accordance with the activity level parameter. FIG. 5 is a flowchart showing an example of a flow of modifying the particle therapy plan performed in accordance with the activity level parameter by the processing circuitry 81 in step S107 of the particle therapy shown in FIG. 3.

Figure 6:
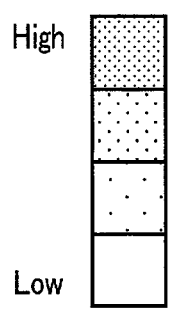
FIG. 6 is a drawing showing a superimposed image in which an activity level parameter is superimposed on a therapy planning CT image according to the first embodiment.
Figure 6:
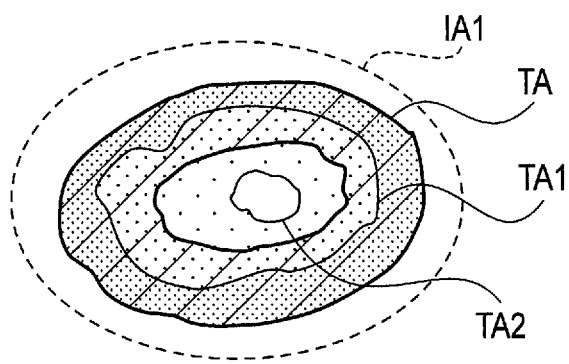

In step S201, the processing circuitry 81 that enables the display controlling function 812 generates superimposed image data by superimposing the activity level parameter on the therapy-planning CT image data (therapy-planning medical image data). It becomes easier to understand if not only the activity level parameter but also the irradiation area and the at-risk organ are superimposed on the image data. The processing circuitry 81 that enables the display controlling function 812 outputs the generated superimposed image data to the display circuitry 84. The display circuitry 84 displays a superimposed image based on the superimposed image data. In other words, the display circuitry 84 displays the activity level parameter distribution superimposed on the therapy-planning CT image data. FIG. 6 is a drawing showing the superimposed image in which the activity level parameter is superimposed on the therapy-planning CT image (therapy planning medical image). In the example shown in FIG. 6, the values of the activity level parameters are schematically expressed by the density of dot-type shading. Suppose the area where the density of dot-type shading is high is an area where the value of the activity level parameter is high. As shown in FIG. 6, suppose the activity level parameter is high on the outside of the tumor area, and low on the inside of the tumor area.

In the generation of superimposed image data, the processing circuitry 81 that enables the display controlling function 812 performs positioning for the activity level parameter distribution and the therapy-planning CT image. For example, if the activity level parameter is a PET image data or an ultrasonic image data, the positioning may be performed based on the shape of an extracted organ. If the activity level parameter is the CT image data, the positioning may be performed through comparing the CT images. In order to perform positioning, the ultrasonic diagnosis apparatus 5 may have a location sensor, for example. The location sensor is arranged in a probe, for example. In advance of the measurement of the activity level parameter, geometrical location correction is performed in the ultrasonic diagnosis apparatus 5. The geometrical location correction is performed through designating a known human body structure on the therapy-planning CT image and the ultrasonic image. With such a configuration, it becomes easier to perform positioning. If the activity level parameter is an MRI image, the positioning may be performed based on a shape of the extracted organ. However, the MRI image has a distortion to some extent. For this reason, the positioning and superimposition may be performed based on the MRI image to which the distortion correction has been performed. To correct the distortion, in the MRI apparatus 4, scanning may be performed under the same conditions using a phantom for distortion distribution measurement, prior to the measurement of the activity level parameter. The distortion correction is performed based on a distribution extracted from the image generated by this scanning.

Since the tumor area is only the area of interest, positioning of the therapy-planning CT image and an image generated by other medical modality may be performed based on a shape of the tumor. At this time, since deviation is more or less acceptable in the area other than the tumor area, the distortion correction becomes unnecessary even if the activity level parameter is the MRI image data.

In step S202, the processing circuitry 81 that enables the active area specifying function 813 specifies the activity of each area in the tumor area based on the activity level parameter distribution. In other words, the processing circuitry 81 that enables the active area specifying function 813 specifies an active area TA1 and a non-active area TA2 in the tumor area TA, as shown in FIG. 6, for example. Put another way, the processing circuitry 81 that enables the active area specifying function 813 separates the tumor area TA into the active area TA1 and the non-active area TA2. In the example shown in FIG. 6, the active area TA1 is a diagonally shaded area, and the non-active area TA2 is an area located inside the active area TA1.

The active area TA1 is an area where the activity level parameter is higher among the areas in the tumor area TA. For example, the active area TA1 is an area where the value of the perfusion information and/or the metabolism information is higher than a predetermined threshold in the tumor area TA. The active area TA1 may be expressed as an area where the sensitivity to particle beams is high in the tumor area TA, or an area where the radiation resistance to particle beams is low in the tumor area TA.

On the other hand, the non-active area TA2 is an area where the activity level parameter is low among the areas of the tumor area TA. For example, the non-active area TA2 is an area other than the active area TA1 in the tumor area TA. For example, the non-active area TA2 is an area where the value of the perfusion information and/or the metabolism information is lower than a predetermined threshold in the tumor area TA. The non-active area TA2 may be expressed as an area where the sensitivity to particle beams is low in the tumor area TA, or an area where the radiation resistance to particle beams is high in the tumor area TA. A predetermined threshold regarding separation into the active area TA1 and the non-active area TA2 is preset and stored in the storage circuitry 86, for example.

This step may be performed prior to step S201. In other words, in the superimposed image, the classification between the active area TA1 and the non-active area TA2 in the tumor area TA may be explicitly shown as in the example of FIG. 6, or may not be explicitly shown.

Figure 7A:
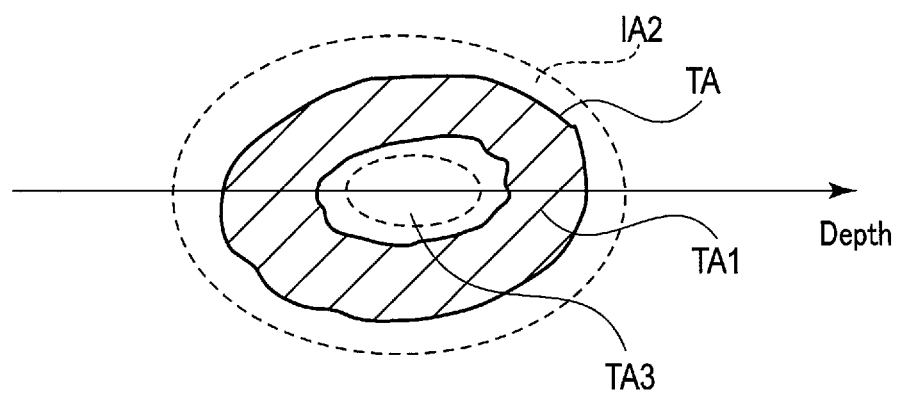
FIG. 7A is a drawing showing an example of temporal planning target volume determined based on the distribution of an active area shown in FIG. 6.

Thereafter, in step S203, the processing circuitry 81 that enables the radiotherapy plan modifying function 814 determines the temporal planning target volume IA2 based on the distribution of the specified active area TA1. Specifically, the processing circuitry 81 that enables the radiotherapy plan modifying function 814 determines the temporal planning target volume IA2, adding a margin to the specified active area TA1 in consideration of patient's body motion and uncertainty of the therapy device. FIG. 7A is a drawing showing an example of a temporal planning target volume IA2 determined based on a distribution of the active area TA1 shown in FIG. 6. In the example shown in FIG. 7A, the temporal planning target volume IA2 based on the active area TA1 is an area between broken lines. The temporal planning target volume IA2 is determined based on the active area TA1 with a margin in consideration of a patient's body motion and uncertainty a treatment device, added. Further in the example shown in FIG. 7A, the temporal planning target volume IA2 is a diagonally shaded area, and the temporal non-target volume IA3 is an area inside the temporal planning target volume IA2.

Thereafter, in step S204, the processing circuitry 81 that enables the radiotherapy plan modifying function 814 determines an administered dose distribution based on the temporal planning target volume IA2 according to the specified active area TA1.

Figure 7B:
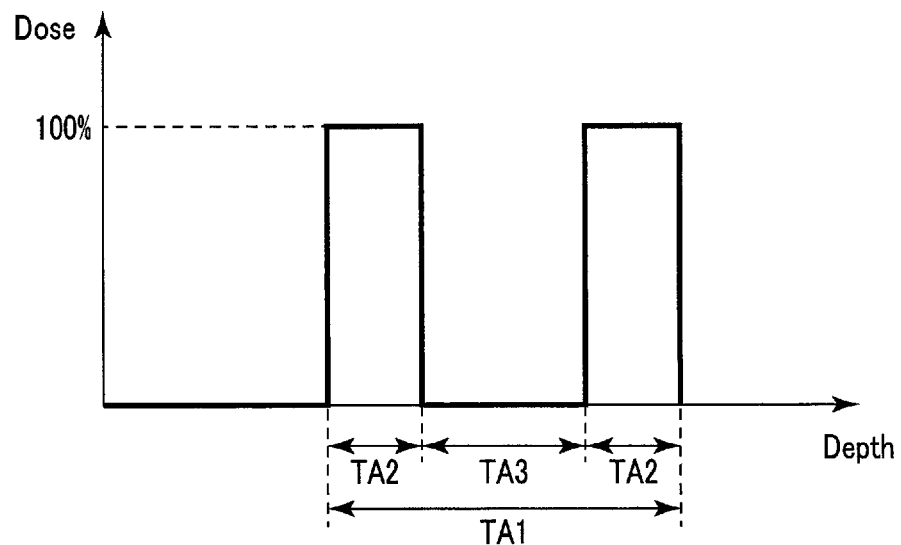
FIG. 7B is an example of an expected administered dose distribution in a depth direction indicated by an arrow shown in FIG. 7A.

First, the processing circuitry 81 that enables the radiotherapy plan modifying function 814 determines an expected administered dose distribution so that a particle beam is administered to the temporal planning target volume IA2, for example. FIG. 7B is an example of the expected administered dose distribution in a depth direction indicated by the arrow shown in FIG. 7A. In the example shown in FIG. 7B, a 100% dose is the expected administered dose distribution per therapy allocated on a time basis.

Figure 7C:
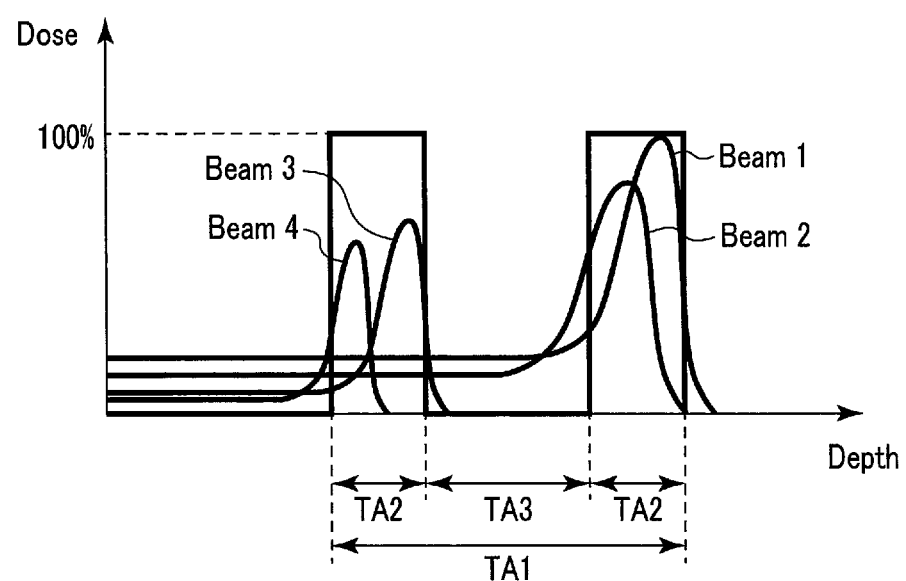
FIG. 7C is an example of a plurality of radiation beams that constitutes an expected administered dose distribution based on the active area shown in FIG. 7B.
Figure 7D:
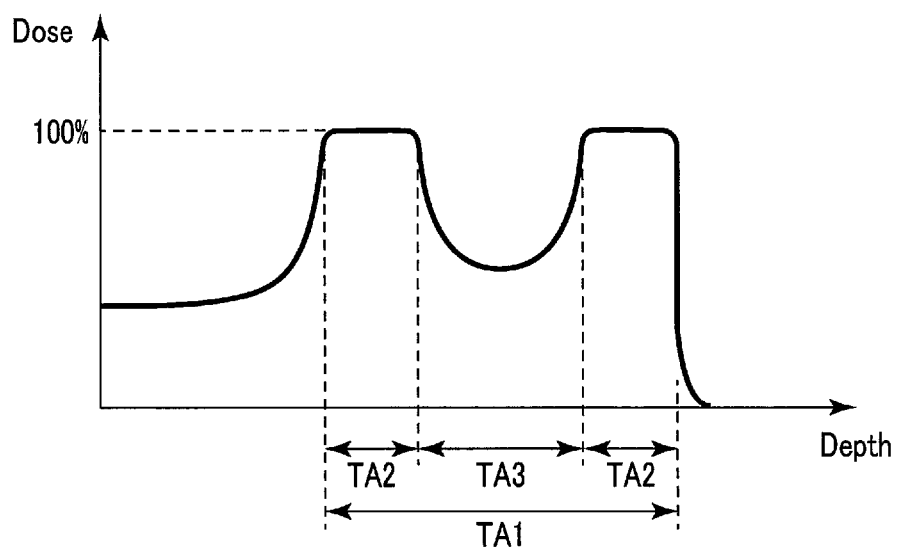
FIG. 7D is an example of spread-out Bragg peaks formed by the plurality of radiation beams shown in FIG. 7C.

Next, the processing circuitry 81 that enables the radiotherapy plan modifying function 814 performs a simulation regarding particle beams based on the expected administered dose distribution in turn based on the distribution of the temporal planning target volume IA2 shown in FIG. 7B. The simulation is similar to the simulation regarding particle beams performed by the particle therapy planning apparatus 7 in step S102, for example. FIG. 7C is an example of a plurality of particle beams that realize the expected administered dose distribution based on the distribution of the temporal planning target volume IA2 shown in FIG. 7B. FIG. 7D is an example of a plurality of spread-out Bragg peaks formed by a plurality of particle beams shown in FIG. 7C.

Thus, the processing circuitry 81 enabling the radiotherapy plan modifying function 814 determines a plurality of particle beams that realize the expected administered dose distribution, namely an administered dose distribution, so that particle beams are administered to the temporal planning target volume IA2, for example. In other words, the processing circuitry 81 enabling the radiotherapy plan modifying function 814 determines the administered dose distribution in such a manner that the irradiation dose to the temporal planning target volume IA2 becomes a predetermined dose, and the irradiation dose to the temporal non-target volume IA3 becomes low. As can be seen from the comparisons shown in FIGS. 4D and 7D, it is possible to reduce the administered dose to normal tissue located in the front of the tumor area by modifying the particle therapy plan based on the activity level parameter, compared to the particle therapy plan produced by the particle therapy planning apparatus 7.

The modification of the administered dose distribution is made by modifying the irradiation conditions, such as the administered dose of particle beams, the number of irradiation times (the number of spot times), and the irradiation direction (irradiation angle), etc. For example, as shown in FIGS. 7A through 7D, the administered dose distribution can be modified by eliminating spot irradiations to the temporal non-target volume IA3. In this case, it is unnecessary to modify the administered dose of particle beams in each irradiation or the other irradiation conditions, such as an irradiation direction, etc., and there are only small modifications to be made in the therapy plan.

Figure 7E:
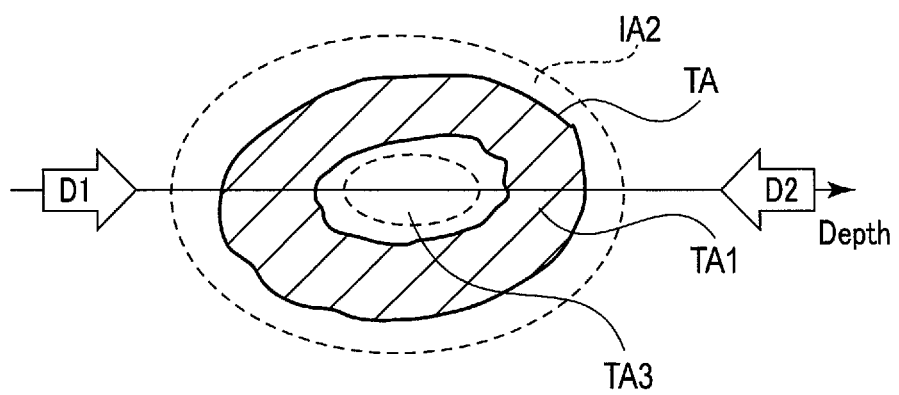
FIG. 7E is a drawing showing the same tumor area TA as that shown in FIG. 7A.

A more appropriate administered dose distribution can be generated by modifying not only the number of irradiation times but also the administered dose and the irradiation direction. FIG. 7E is a drawing showing the same temporal planning target volume IA2 as that shown in FIG. 7A. FIGS. 7A through 7D illustrate the therapy plan using particle beams in the irradiation direction D1 shown in FIG. 7E. In this case, as shown in FIGS. 7C and 7D, a dose is accumulated in an area shallower than the temporal planning target volume IA2 because of overlapping particle beams. In such cases, as shown in FIG. 7E, it is preferable to modify the therapy plan so that the particle beams are emitted in a direction D2, which differs from the original irradiation direction D1.

In the following, a case where the therapy plan is modified so as to emit particle beams in the irradiation direction D2 opposite to the irradiation direction D1 will be described as an example. Even in this case, since the tumor area TA, the active area TA1, and the temporal planning target volume IA2, the temporal non-target volume IA3 are the same between FIGS. 7A and 7E, the expected administered dose distribution is still the same as that in FIG. 7B.

FIG. 7F is a drawing showing an expected administered dose distribution on which a plurality of particle beams are superimposed in the irradiation direction D1 and the irradiation direction D2 shown in FIG. 7E. As shown in FIG. 7F, the therapy plan is modified in such a manner that an administered dose is concentrated on the temporal planning target volume IA21 in the front with respect to the irradiation direction D1, and the temporal planning target volume IA22 in the front with respect to the irradiation direction D2. Specifically, a spread-out Bragg peak is formed in the temporal planning target volume IA21 by a plurality of particle beams in the irradiation direction D1, and a spread-out Bragg peak is formed in the temporal planning target volume IA22 by a plurality of particle beams in the irradiation direction D2.

FIG. 7G is an example of spread-out Bragg peaks formed by the plurality of particle beams shown in FIG. 7F. As shown in FIG. 7G, it is possible to reduce an administered dose to the area TB1 in the front of the temporal planning target volume IA21 by spreading the irradiation direction, compared to the case shown in FIG. 7D where the particle beams are emitted in one direction of D1. It is also possible to greatly reduce the administered dose to the temporal non-target volume IA3 which is located deeper when seen from both the temporal planning target volume IA21 and temporal planning target volume IA22.

In other words, the processing circuitry 81 that enables the radiotherapy plan modifying function 814 determines the administered dose distribution so as not to irradiate the temporal non-target volume IA3 with particle beams, for example. For example, as shown in FIG. 7D, the administered dose distribution according to the modified particle therapy plan, the administered dose to the planning target volume IA1 has been partially decreased. However, this area corresponds to the temporal non-target volume IA3. In other words, the area is an area in which the non-active area TA2 is dominant, which has fewer effects on cancer cells even when it is irradiated with particle beams.

In step S205, the modified administered dose distribution, etc. is checked by the planner or by the particle therapy planning apparatus 7 in a manner similar to step S102. The checking of the modified particle therapy plan may be performed in the particle therapy support apparatus 8. After the plan is authorized during the checking process, the storage circuitry 86 of the particle therapy support apparatus 8 stores the modified particle therapy plan and the modified administered dose distribution. Furthermore, the particle therapy support apparatus 8 transfers the modified particle therapy plan to the particle therapy apparatus 9. Thereafter, the modification of the particle therapy plan which is performed in accordance with the activity level parameter is finished. After the modification is finished, the processing proceeds to step S108 shown in FIG. 3.

In step S108, the particle therapy using the particle therapy apparatus 9 is performed based on the produced particle therapy plan, the modified particle therapy plan, or an additional particle beam administering plan. The additional particle beam administering plan will be described later. In the particle therapy, urination and defecation are controlled prior to each therapy session.

In the particle therapy performed based on the modified particle therapy plan, a sufficient dose of a particle beam is not administered to the temporal non-target volume IA3 in the planning target volume IA1. However, the distribution of the active area TA1 and the non-active area TA2 in the planning target volume IA1 changes during the particle therapy, which is performed multiple times. As described above, the particle therapy plan may be modified for each therapy in accordance with the measured activity level parameter. In other words, according to the present technology, even in any area in the planning target volume IA1, the particle therapy plan can be modified so as to perform irradiation of an adequate dose of particle beam upon the time when the non-active area TA2 changes to the active area TA1 during particle therapy performed multiple times.

Specifically, before a particle therapy is performed multiple times based on the particle therapy plan, the processing circuitry 81 that enables the parameter obtaining function 811 re-specifies an active area and a non-active area in accordance with the active parameter that has been changed with time. The processing circuitry 81 that enables the radiotherapy plan modifying function 814 determines an administered dose distribution so that a cumulative dose in each area in the planning target volume IA1 approximately matches a target dose. In other words, the processing circuitry 81 that enables the radiotherapy plan modifying function 814 changes a location and a width of a spread-out Bragg peak in the tumor area in the radiotherapy spanning multiple days, in accordance with a temporal change of the activity level (sensitivity). The processing circuitry 81 that enables the radiotherapy plan modifying function 814 changes the location and the width of the spread-out Bragg peak in the tumor area so as to modify a distribution of a particle beam dose applied to the planning target volume (a shape of the spread-out Bragg peak). Specifically, the processing circuitry 81 that enables the radiotherapy plan modifying function 814 modifies a dose distribution in the planning target volume so that a plurality of spread-out Bragg peaks are formed. The plurality of spread-out Brag peaks may be expressed as a spread-out Bragg peak having a plurality of peaks. The temporal change of the activity level (sensitivity) may be obtained by re-measuring the activity level parameter including the perfusion information and/or metabolism information, for example. The temporal change of the activity level (sensitivity) may be obtained by predicting the activity level based on, for example, a value obtained in the past, the number of days passed, a cell-division cycle, etc. The prediction may be made based on data of the same patient (subject) or data of a plurality of patients. The data used to make a prediction may be accumulated in associated with a body part, a disease case, an age, and radiation quality of radiation, etc.

In step S109, the processing circuitry 81 that enables the radiotherapy plan modifying function 814 accumulates the radiation quality given at each therapy for each area in the patient's body, and calculates a cumulative value of the administered dose (a cumulative dose). Alternatively, the processing circuitry 81 may accumulate a value obtained by multiplying the activity level parameter in each area with the dose administered each time for each area in the patient's body, and calculate a cumulative value of treatment effectiveness (a cumulative treatment effectiveness 1). Furthermore, the processing circuitry 81 may accumulate a value obtained by further multiplying a relative biological effectiveness (RBE) determined by characteristics of an irradiation beam and sensitivity of each tissue in each area with the dose administered each time for each area in the patient's body, and calculate a cumulative value of treatment effectiveness different from the foregoing treatment effectiveness (a cumulative treatment effectiveness 2). The processing circuitry 81 that enables the display controlling function 812 generates superimposed image data by superimposing one of a cumulative dose calculated, a cumulative treatment effectiveness 1, or a cumulative treatment effectiveness 2 for each area in the patient's body, or a combination thereof, on the therapy-planning CT image (therapy-planning medical image). The processing circuitry 81 that enables the display controlling function 812 outputs the generated superimposed image data to the display circuitry 84. The display circuitry 84 displays a superimposed image based on the superimposed image data. In other words, the display circuitry 84 displays the therapy-planning CT image data on which one of the total dose of particle beams irradiated to each area in the patient's body, the cumulative treatment effectiveness 1, or the cumulative treatment effectiveness 2, or the combination thereof is superimposed. A user, such as a doctor, can check whether or not a sufficient dose is administered to each area of the planning target volume IA1 by checking this superimposed image.

The superimposed image displayed in this step may further include the distribution of the activity level parameter and/or the distribution of the active area TA1. It becomes easier to understand if the irradiation area and the at-risk organ are also superimposed on the image data. However, as the simultaneous display of all the information items would make it difficult to interpret the superimposed image, it would be desirable to display only the information items selected by a radio button, for example, on the superimposed image.

In step S110, after the particle therapy of the predetermined number of times is completed, the processing circuitry 81 that enables the radiotherapy plan modifying function 814 determines whether or not to produce an additional particle beam administering plan. This determination is made based on an output of the input circuitry 85 in accordance with user's input, for example. The user, such as a doctor, can determine whether or not to produce an additional particle beam administering plan based on the superimposed image displayed in step S109. If information indicating that there is an area where the cumulative dose, the cumulative treatment effectiveness 1, or the cumulative treatment effectiveness 2 is low is available, the user, such as a doctor determines that an additional particle beam administering plan should be produced based on such information. Thereafter, if it is determined that an additional particle beam administering plan is produced, the processing proceeds to step S111; if not, the processing proceeds to step S112. Herein, whether or not to produce the additional particle beam administering plan is determined after a predetermined particle therapy is finished; however, that can be determined after the particle therapy of the predetermined number of times is finished.

There may be a case in which a follow-up is performed without additionally administering particle beams after the particle therapy of the predetermined number of times is completed. For example, there may be case where an area in which the activity level parameter did not once become high during a session of particle therapy will never become active in the future. In such a case, it should be checked whether or not the activity level parameter becomes high once a week at first, once a few weeks in a few months later, and once a few months in a year later, for example. If the activity is not high, it is least likely that tumor cells rapidly replicate; thus, a therapy can be performed when a change of the activity level parameter is observed.

This determination may be made based on a comparison between a planned dose according to the particle therapy plan and a cumulative dose calculated for each area of the planning target volume IA1. For example, when a ratio of the cumulative dose to the planned dose is less than a predetermined threshold, the processing circuitry 81 that enables the radiotherapy plan modifying function 814 may determine to produce an additional particle beam administering plan. The predetermined threshold regarding the ratio may be preset and stored in the storage circuitry 86, for example. Although the example where the therapy plan is modification based on a comparison between the cumulative dose and the planned dose has been described herein, the modification may be made based on a comparison between a cumulative treatment effectiveness 1 or a cumulative treatment effectiveness 2 to a planning cumulative treatment effectiveness 1 or a planning cumulative treatment effectiveness 2. However, since the aforementioned cumulative treatment effectiveness 1 and cumulative treatment effectiveness 2 are totally new concepts, it is necessary to accumulate experiences so as to identify a planning cumulative treatment effectiveness 1 or a planning cumulative treatment effectiveness 2 appropriately.

In step S111, the particle therapy planning apparatus 7 or the particle therapy support apparatus 8 produces an additional particle beam administering plan in a manner similar to step S102 or step S107, for example. The additional particle beam administering plan is produced so as to give particle beams to an area where a cumulative dose is low, for example. Thereafter, the processing returns to step S108, and a particle therapy, etc. is performed based on the additional particle beam administering plan.

In step S112, the processing circuitry 81 that enables the radiotherapy plan modifying function 814 determines whether or not to finish the particle therapy. In this determination, it is determined that the particle therapy should be finished when the total particle beam administered dose (a total dose) to each area of the planning target volume IA1 reaches a predetermined dose, for example. In other words, the particle therapy plan is modified so that the particle therapy is repeated until the total dose to each area of the planning target volume IA1 reaches a predetermined dose. Thereafter, when it is determined that the particle therapy is finished, the processing relating to the modification of the particle therapy plan is finished; when it is determined that the particle therapy is not finished, the processing returns to step S103.

This determination may be made based on the output of the input circuitry 85 in accordance with a user's input, or at a predetermined cycle or timing. The particle therapy is performed multiple times. The particle therapy is performed once a day, for example. The particle therapy is performed five days a week only on weekdays, for example. The particle therapy is performed continuously for six weeks, for example. In other words, the particle therapy is performed 30 times in total, for example. A dose of one-time radiation, the number of times, a total dose, etc. may be set as appropriate in accordance with each disease case. The threshold value, etc. used for the determination should be preset and stored in the storage circuitry 86, etc. If the cycle or timing of the modification of the particle therapy plan is predetermined, the determination is not necessarily made.

Thus, in the particle therapy support apparatus 8 according to the present embodiment, the processing circuitry 81 that enables the radiotherapy plan modifying function 814 modifies the particle therapy plan produced by the particle therapy planning apparatus 7 in accordance with the activity level parameter. According to the configuration, it is possible to change the irradiation area and the administered dose distribution of particle beams in the particle therapy, in accordance with the activity level parameter distribution. The activity level parameter may be expressed as a parameter regarding radiation resistance of the planning target volume IA1, or a parameter-according to sensitivity to particle beams in the tumor area. For example, the activity level parameter includes the perfusion information and/or the metabolism information of each area of the planning target volume IA1. In other words, according to the present technology, it is possible to irradiate the active area having high sensitivity to particle beams in the planning target volume IA1 with particle beams, thereby improving efficiency in the use of particle beams in the particle therapy. In other words, as for the non-active area where the sensitivity to particle beams is low in the planning target volume IA1, the particle beam dose distribution is modified so as to reduce the dose administered to that area, thereby reducing a dose of particle beams that has less effect to cancer tissue when administered. This reduction can lead to reduction of a dose to a normal body part in the vicinity of the planning target volume IA1, particularly a normal body part between a beam entrance point and the planning target volume IA1. The modification of the particle therapy plan is performed at predetermined timing when the activity level parameter is re-obtained. In other words, according to the present technology, it is possible to update the irradiation area and the administered dose distribution of particle beams in accordance with a temporal change of the active area in the tumor area.

Widely known is the identification of a patient's body shape or a shape of a tumor from a CT image or an MR image, etc., and to modify a therapy plan based on the body shape or the shape of the tumor at the time when the plan was produced. The therapy based on the modification of plan is called an adaptive radiation therapy (ART). It is recommended to perform an adaptive radiation therapy also in a therapy where the technology according to the present embodiment is adopted. The therapy where the technology according to the present embodiment is adopted greatly differs from an adaptive radiation therapy where the technology according to the present embodiment is not adopted, as this therapy is effective even before an adaptive radiation therapy is performed, in other words, even when a shape of a tumor is unchanged. There following advantages will be accrued if the technology according to the present embodiment is adopted, compared to the adaptive radiation therapy.

According to the technology of the present embodiment, it is possible to reduce a dose to a normal body part through inhibiting irradiation to an area where radiation resistance is high, namely an area where particle beam irradiation is less effective to cancer tissue, in accordance with a parameter regarding radiation resistance.

With the technology according to the present embodiment, through concentrating a dose on an area where the radiation resistance is low, it is possible to treat a tumor effectively, in other words, with a dose smaller than that required in an adaptive radiation therapy. According to the technology of the present embodiment, an area where radiation resistance is high is treated when the radiation resistance becomes low. With this therapy strategy, it is possible to conduct a therapy with a lower total dose.

Second Embodiment

The radiotherapy planning apparatus, the radiotherapy apparatus, and the radiotherapy planning method according to this embodiment will be described below with reference to the accompanying drawings. Herein, differences between the first embodiment and the second embodiment will be mainly described. Note that in the following description, the same reference numerals denote constituent elements having the same or almost the same functions as those included in this embodiment, and a duplicate description will be made only when required.

Suppose a lethal effect is brought about by, for example, a particle therapy to the tumor cells in the active area TA1 around the non-active area TA2. At this time, blood flows are no longer stolen in the peripheral area which has been the active area TA1, and the blood flowing into the inner area, which has been the non-active area TA2, increases, and the activity level of the cells is rapidly increased. If the active level parameter is identified based on the perfusion information, when the activity level parameter is re-measured with this state, the internal area which has become an active area after the particle beam irradiation is specified as a highly active area. At the same time, however, there is a possibility that the outer area to which a sufficient dose of particle beams has been administered may be specified as an active area where the activity is still high. In other words, there is a possibility that the active area may include cells to which a lethal effect has been produced.

Thus, in the present embodiment, a particle therapy support apparatus that modifies a particle therapy plan in accordance with a cumulative dose calculated for each area of the tumor area TA in addition to the distribution of the active area TA1 will be described as an example, on the assumption that radiation resistance of the tumor area TA changes along with the change in the surrounding environment of cells.

Figure 8:
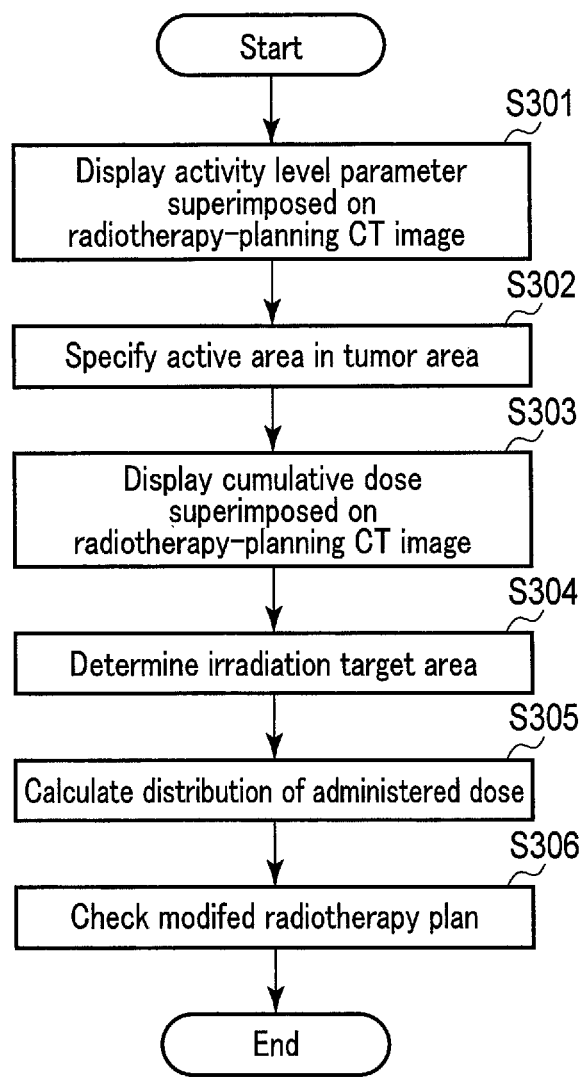
FIG. 8 is a flowchart showing another example of a flow of a modification of a radiotherapy plan performed in accordance with an activity level parameter in the radiotherapy shown in FIG. 3.

FIG. 8 is a flowchart showing another example of a flow of a modification of a particle therapy plan performed in accordance with an activity level parameter in step S107 of the particle therapy shown in FIG. 3.

Steps S301, S302, and S306 are the same as steps S201, S202, and S205 shown in FIG. 5, respectively.

Figure 9:
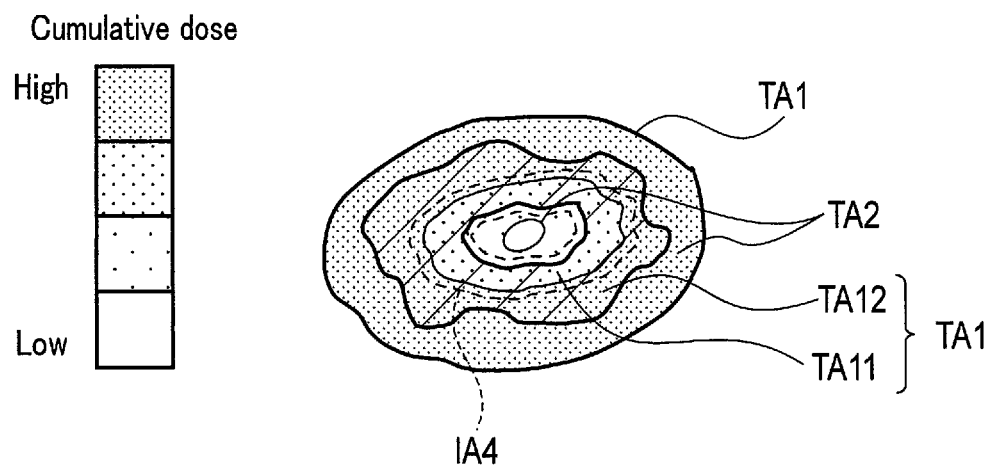
FIG. 9 is a drawing showing a superimposed image which is obtained by superimposing a cumulative dose on a therapy planning CT image according to a second embodiment.

In step S303, similarly to step S109 shown in FIG. 3, for example, the processing circuitry 81 that enables the display controlling function 812 according to the present embodiment superimposes the cumulative dose calculated for each area in the patient's body on the therapy-planning CT image, thereby generating superimposed image data. The display circuitry 84 displays a superimposed image based on the superimposed image data. FIG. 9 is a drawing showing the superimposed image which is obtained by superimposing the cumulative dose on the therapy-planning CT image according to the present embodiment. In the example shown in FIG. 9, the value of the cumulative dose is schematically expressed by the density of dot-type shading. Suppose the area where the density of dot-type shading is high is an area where the value of the cumulative dose is high. Further in the example shown in FIG. 9, the active area TA1 is a diagonally shaded area, and the non-active area TA2 is an inner and outer area of the active area TA1. In the example shown in FIG. 9, the inside of the active area TA1 contains the active area TA11 where the cumulative dose is low and the active area TA12 where the cumulative dose is high.

In step S304, the processing circuitry 81 that enables the radiotherapy plan modifying function 814 according to the present embodiment determines a temporal planning target volume IA4 based on an area where the value of the cumulative dose is lower than a threshold in the active area TA1. Specifically, the processing circuitry 81 that enables the radiotherapy plan modifying function 814 determines the temporal planning target volume IA4, adding a margin to the specified active area TA11 where the cumulative dose is low in consideration of patient's body motion and uncertainty of the therapy device. processing circuitry 81 radiotherapy plan modifying function 814 cumulative dose The processing circuitry 81 that enables the radiotherapy plan modifying function 814 may be configured to warn the user such as a doctor when the active area TA12, where the cumulative dose is high, is detected. The warning may be made through an announcement or sound such as warning sound, or by displaying a warning.

The separation of the active area TA1 into the active area TA11 where the cumulative dose is low and the active area TA12 where the cumulative dose is high may be performed in accordance with a determination made by a doctor, etc. who sees the superimposed image on which the cumulative dose regarding each area of the tumor area is superimposed.

The superimposed image displayed in this step may further include the distribution of the activity level parameter.

In step S305, similarly to step S204 in FIG. 5, the processing circuitry 81 that enables the radiotherapy plan modifying function 814 determines an administered dose distribution based on the temporal planning target volume IA4 according to the specified active area TA1 and the cumulative dose.

Thus, the display circuitry 84 according to the present embodiment is caused, prior to a particle therapy in each therapy session, to display a superimposed image in which the cumulative dose calculated for each area in the patient's body is superimposed on the therapy-planning CT image. First, the processing circuitry 81 that enables the radiotherapy plan modifying function 814 modifies the particle therapy plan in such a manner that particle beams are not administered to the active area having a value of the cumulative dose larger than a predetermined threshold (the active area TA12 having a high cumulative dose) in the planning target volume IA1, for example. In other words, the processing circuitry 81 that enables the radiotherapy plan modifying function 814 modifies the particle therapy plan so that particle beams are administered to the active area having a value of the cumulative dose smaller than a predetermined threshold (the active area TA11 having a low cumulative dose) in the planning target volume IA1, for example. According to this configuration, in addition to the above-described advantageous effects, there is an advantageous effect of allowing a user, such as a doctor, to easily discern an area to which a dose required for a therapy has already been administered, such as an original planned dose, etc. in advance of the therapy. For this reason, the user such as a doctor can stop irradiation to the area to which a dose required for a therapy has already been administered even when the activity level parameter is still high. It is also possible to inhibit excessive irradiation of particle beams to a normal body part located in the front of the tumor area (the irradiation side) through inhibiting the irradiation of particle beams to the area where the tumor cells have already become extinct. In the second embodiment, a case where the particle therapy plan is modified in accordance with the cumulative dose has been mainly described; however, the particle therapy plan may be modified based on the cumulative treatment effectiveness 1 or the cumulative treatment effectiveness 2.

First Modification

The radiotherapy planning apparatus, the radiotherapy apparatus, and the radiotherapy planning method according to this modification will be described below with reference to the accompanying drawings. Herein, differences between the first embodiment and the second embodiment will be mainly described. Note that in the following description, the same reference numerals denote constituent elements having the same or almost the same functions as those included in the first embodiment, and a duplicate description will be made only when required.

In the first embodiment, the particle therapy support apparatus 8 that separates the tumor area TA into the active area TA1 and the non-active area TA2, and modifies the particle therapy plan so as not to apply particle beams to the non-active area TA2 as much as possible, is described as an example. However, the modification of the particle therapy plan in accordance with the activity level parameter is not limited to this example. There are various levels of the sensitivity to particle beams in each area of the tumor area TA, namely the activity levels. Accordingly, in the present modification, the particle therapy support apparatus 8 that modifies a particle therapy plan so as not to give particle beams to the non-active area TA2 as much as possible in accordance with an activity level will be described as an example.

In the particle therapy support apparatus 8 according to the present modification, the processing circuitry 81 that enables the radiotherapy plan modifying function 814 determines a ratio of the expected administered dose to the planned dose in each therapy session defined by the original particle therapy plan. The ratio is determined in accordance with the activity level parameter. The processing circuitry 81 that enables the radiotherapy plan modifying function 814 determines the expected administered dose distribution based on the planned dose and the ratio.

Herein, the flow of the modification of the particle therapy plan according to the present modification will be described in detail with reference to FIG. 5. Steps S201 through step S203, and step S205 are the same as those in the first embodiment.

Thereafter, in step S204, the processing circuitry 81 that enables the radiotherapy plan modifying function 814 determines an administered dose distribution based on the temporal planning target volume. IA1, adding a margin to the specified active area TA1 in consideration patient's body motion and uncertainty, etc. of the therapy device.

Figure 10:
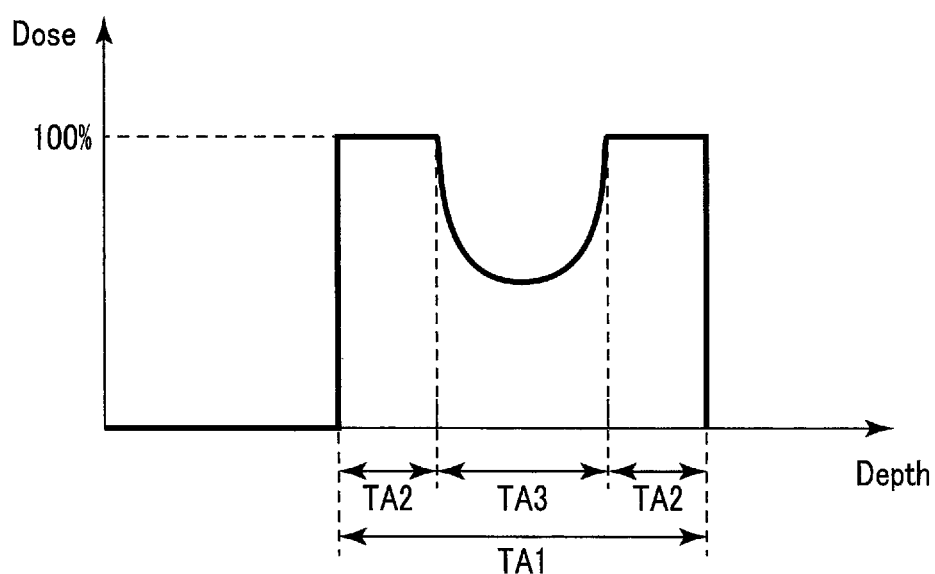
FIG. 10 is another example of an expected administered dose distribution in a depth direction indicated by an arrow shown in FIG. 7A.

First, the processing circuitry 81 that enables the radiotherapy plan modifying function 814 determines a ratio of the expected administered dose to the planned dose defined by the original particle therapy plan. FIG. 10 is another example of an expected administered dose distribution in a depth direction indicated by an arrow shown in FIG. 7A.

For example, the processing circuitry 81 that enables the radiotherapy plan modifying function 814 determines the ratio regarding the temporal planning target volume IA2 is 100%. In other words, as shown in FIG. 10, the processing circuitry 81 that enables the radiotherapy plan modifying function 814 determines the expected administered dose distribution so that 100% particle beam of the original planned dose is administered to the temporal planning target volume IA2, for example.

On the other hand, for example, the processing circuitry 81 that enables the radiotherapy plan modifying function 814 determines that the ratio regarding the temporal non-target volume IA3 falls under the range of 0 to 100% in accordance with a value of the activity level parameter. In other words, as shown in FIG. 10, the processing circuitry 81 that enables the radiotherapy plan modifying function 814 determines the expected administered dose distribution so that particle beams at a dose between 0 to 100% of the originally-planned dose are administered to the temporal non-target volume IA3 in accordance with, for example.

Next, similar to the first embodiment, the processing circuitry 81 that enables the radiotherapy plan modifying function 814 determines an administered dose distribution based on the expected administered dose distribution shown in FIG. 10.

The ratio of the expected administered dose distribution to the original planned dose can be determined in accordance with the activity level parameter not only for the temporal non-target volume IA3 but also for the temporal planning target volume IA2. Although the example where the 100% dose of the original plan is determined for the temporal planning target volume IA2 is described in the above, the ratio of the expected administered dose distribution to the original planned dose for the temporal planning target volume IA2 may be determined so that a 100% dose of the original planned dose is administered.

The administered dose distribution in accordance with the activity level parameter may be determined by separating the temporal planning target volume IA2 into two or more areas in accordance with the activity level parameter. In this case, the processing circuitry 81 that enables the active area specifying function 813 separates the temporal planning target volume IA2 into two or more areas, for example. The processing circuitry 81 that enables the radiotherapy plan modifying function 814 determines the expected administered dose distribution, etc. in accordance with a plurality of ratios of the multiple areas.

Thus, the particle therapy support apparatus 8 according to the present modification modifies a particle therapy plan so that particle beams are administered at a dose in accordance with an activity level of each area in the temporal planning target volume IA2. For example, the particle therapy support apparatus 8 modifies the particle therapy plan in such a manner that, as shown in FIG. 10, a 0 to 100% dose of the original planned dose is administered in accordance with the value of the activity level parameter to the temporal non-target volume IA3, which was supposed to be administered with a 0% dose of the original planned in the example shown in FIG. 7B. According to the configuration, the efficiency in the use of particle beams in a particle therapy can be thereby further improved.

The technology according to the present modification may be combined with not only the technology according to the first embodiment but also with the technology according to the second embodiment.

Second Modification

The radiotherapy planning apparatus, the radiotherapy apparatus, and the radiotherapy planning method according to this modification will be described below with reference to the accompanying drawings. Herein, differences between the first embodiment and the second embodiment will be mainly described. Note that in the following description, the same reference numerals denote constituent elements having the same or almost the same functions as those included in the first embodiment, and a duplicate description will be made only when required.

In the first embodiment, the particle therapy support apparatus 8 that modifies a particle therapy plan so that particle beams are administered to the temporal planning target volume IA2 with priority is described as an example. However, the modification of the particle therapy plan in accordance with the activity level parameter is not limited to this example. In the present modification, the particle therapy support apparatus 8 that modifies a particle therapy plan so that particle beams are administered to the temporal non-target volume IA3 with priority will be described as an example.

The processing circuitry 81 that enables the radiotherapy plan modifying function 814 according to the present modification determines an irradiation target area and an administered dose distribution based on a distribution of a specified temporal non-target volume IA3. Specifically, the processing circuitry 81 that enables the radiotherapy plan modifying function 814 determines an irradiation target area and an administered dose distribution so as to cause a lethal effect upon tumor cells of the temporal non-target volume IA3.

According to this configuration, it is possible to give particle beams at a high dose to the temporal non-target volume IA3 having high particle resistance to an extent that causes a lethal effect upon tumor cells, and to inhibit an administered dose for the temporal planning target volume IA2 having high sensitivity to particle beams. In other words, according to the present technology, an advantageous effect of conducting a treatment in a shorter time than a conventional treatment time can be achieved through increasing a dose to the temporal non-target volume IA3. However, this technology is only applicable when there is no at-risk organ in the vicinity of the planning target volume IA1, as the technology has a risk of increasing a dose to normal tissue in the vicinity of the planning target volume IA1.

The technology according to the present modification may be combined with not only the technology according to the first embodiment but also with the technology according to the second embodiment.

In each of the foregoing embodiments and modifications, an example where a modification of a particle therapy plan is made in the particle therapy support apparatus 8; however, the foregoing embodiments and modifications are not limited to this example. For example, a part or all of the functions enabled by executing the radiotherapy support program by the processing circuitry 81 may be realized by a medical modality that measures activity level parameters, the particle therapy planning apparatus 7, the particle therapy apparatus 9, or a server provided externally to the particle therapy system 100. For example, a part or all of the processing circuitry 81 may be provided in a medical modality that measures activity level parameters, the particle therapy planning apparatus 7, the particle therapy apparatus 9, or a server provided externally to the particle therapy system 100. In other words, the particle therapy apparatus 9 in which a part or all of the processing circuitry 81 is provided with an irradiation unit that irradiates the tumor area with particle beams based on a particle therapy plan made or a particle therapy plan modified. Advantageous effects similar to those described above can be achieved by such configurations. For example, if all of the processing circuitry 81 is provided in a server in turn provided externally to the particle therapy system 100, a measured activity level parameter is transmitted to the server. For example, the particle therapy planning apparatus 7 can display an image based on the image data by obtaining image data in which an activity level parameter is superimposed on a therapy-planning CT image (therapy-planning medical image), similarly to the foregoing embodiments and modifications. The particle therapy apparatus 9 can obtain the modified particle therapy plan from the server, and perform a particle therapy based on the modified particle therapy plan, similar to each of the foregoing embodiments and modifications.

In each of the foregoing embodiments and modifications, the particle therapy support apparatus 8 modifies a particle therapy plan produced by the particle therapy planning apparatus 7 in accordance with an activity level parameter, and finally determines a distribution of a particle beam administered dose (dose) in a planning target volume IA1. However, the foregoing embodiments and modifications are not limited thereto. For example, the particle therapy planning apparatus 7 and the particle therapy support apparatus 8 may be integrally configured. The particle therapy support apparatus 8 may determine a dose distribution in a planning target volume IA1 in accordance with an activity level parameter in the planning target volume IA1, regardless of a modification of a particle therapy plan. In this case, the dose distribution in the planning target volume IA1 may be determined by the particle therapy planning apparatus 7, by the particle therapy apparatus 9, or by other computer. For example, in order to give a 100% dose to the temporal planning target volume IA2, and not to give any dose to the temporal non-target volume IA3 as much as possible, a good result can be obtained if re-planning is performed through resetting the conditions of the particle therapy for the planning target volume IA1. However, it is possible to achieve a dose distribution close to a desired condition without performing re-planning, and through following an original therapy plan that defines ceasing irradiation of the temporal non-target volume IA3 with a proton ray beam having a peak, and adjusting a strength of the proton ray beam irradiated to the temporal planning target volume IA2 located in the front of a peak area of the proton ray beam. In this case, as re-planning is not necessary, it is possible to save the considerable time required for modifying the plan. In those configurations, the particle therapy support apparatus 8 is provided with a therapy plan producing unit that determines a dose distribution in a planning target volume IA1 in accordance with an activity level parameter distribution in the planning target volume IA1, and produces a particle therapy plan. According to those configurations, it is possible to produce a particle therapy plan in accordance with the planning of a total particle beam administered dose (total dose) to a tumor area and an activity level parameter distribution. An originally-planned particle therapy plan corresponds to a particle therapy plan modified in each of the foregoing embodiments and modifications, and includes a dose distribution in a planning target volume IA1. The planning of a total dose to a planning target volume IA1 can be set as appropriate in accordance with a disease case, etc. In other words, an advantageous effect of simplifying the process of producing a particle therapy plan can be achieved in addition to the above-described advantageous effects.

In each of the foregoing embodiments and modifications, the particle therapy support apparatus 8 determines the temporal planning target volume IA2 and the temporal non-target volume IA3 in accordance with the activity level parameter distribution in the planning target volume IA1. However, the foregoing embodiments and modifications are not limited thereto. The particle therapy support apparatus 8 can determine to give a 100% dose to an area having a high activity level parameter, a 0% dose to an area having a low activity level parameter, or determine an appropriate dose to an area having an intermediate activity level parameter in accordance with the parameter.

In each of the foregoing embodiments and modifications, the particle therapy support apparatus 8 determines a particle beam irradiation area and a dose distribution in accordance with the activity level parameter distribution in the planning target volume IA1. However, the foregoing embodiments and modifications are not limited thereto. The particle therapy support apparatus 8 may determine a particle beam irradiation area and a dose distribution in accordance with the activity level parameters obtained throughout multiple organs. With such a configuration, it is possible to perform a particle therapy on a plurality of tumor areas distribution over multiple organs. Furthermore, according to the technology of the second embodiment for example, it is possible to determine an irradiation area and a dose distribution so as to exclude an at-risk organ from a specified active area.

In the particle therapy support apparatus 8 according to each of the foregoing embodiments and modifications, the irradiation target area and a dose distribution may be selected from preset patterns. For example, a plurality of preset active area patterns and a plurality of preset dose distributions are stored in the storage circuitry 86. Suppose the plurality of active area patterns are prepared in accordance with a planned dose, a shape of an active area, a size of an active area, for example. Each of the plurality of active area patterns is stored, and respectively associated with a plurality of administered dose distributions calculated in advance. In the determination of the irradiation target area for example, the processing circuitry 81 that enables the radiotherapy plan modifying function 814 selects an active area pattern similar to the distribution of the specified temporal planning target volume IA2. The processing circuitry 81 that enables the radiotherapy plan modifying function 814 modifies the particle therapy plan based on an administered dose distribution according to the selected active area pattern. At this time, the processing circuitry 81 that enables the radiotherapy plan modifying function 814 may correct the administered dose distribution according to the selected active area pattern. The correction of the administered dose distribution is performed in accordance with a ratio or difference between the size of the specified temporal planning target volume IA2 and the size of the selected active area pattern. The correction of the administered dose distribution is performed in accordance with a ratio or difference between a planned dose according to the original particle therapy plan and a planned dose associated with the selected active area pattern. With such a configuration, in addition to the above-described effects, an effect of mitigating calculation loads at the time of modifying a particle therapy plan can be achieved.

In the particle therapy support apparatus 8 according to each of the foregoing embodiments and modifications, the modification of the particle therapy plan may be made in accordance with a result of a further plurality of activity level parameters. For example, the processing circuitry 81 that enables the parameter obtaining function obtains an activity level parameter based on perfusion from the radiotherapy-planning X-ray CT apparatus 6, and obtains, from the PET apparatus 1 or the PET-CT apparatus 3, an activity level parameter based on viability according to FDG-PET. The processing circuitry 81 that enables the radiotherapy plan modifying function 814 determines an irradiation target area and an administered dose distribution in accordance with an activity level parameter distribution based on perfusion and a result of the activity level parameter based on the viability. With this configuration, it is possible to modify the therapy plan based on the values of two activity level parameters for each area of a planning target volume IA1, thereby improving a reliability of the modified plan and further improving efficiency in using particle beams in the particle therapy.

The processing circuitry 81 in the particle therapy support apparatus 8 according to each of the foregoing embodiments and modifications may be configured to execute a sensitivity adjustment function that controls surrounding conditions, such as a pH value or a temperature, etc. of a tumor area. For example, the processing circuitry 81 that enables the sensitivity adjustment function generates a control signal to control sensitivity to particle beams in a tumor area. At this time, the particle therapy system 100 further includes a sensitivity adjustment apparatus that operates in accordance with the control signal. The sensitivity adjustment apparatus is configured to perform thermal processing that heats a tumor area in synchronization with irradiation of particle beam, for example. The sensitivity adjustment apparatus heats a tumor area at, for example, around 43 to 45° C. by the thermal processing. The thermal processing may be performed by a method in accordance with a size or a depth (a distance from the body surface) of the tumor area. The sensitivity adjustment apparatus may be configured to lower a pH value of a cell in the tumor area in synchronization with the application of particle beams, for example. With this configuration, it is possible to adjust, for example, the size of the active area and timing when the non-active area changes to the active area. In other words, it is possible to modify the particle therapy plan in accordance with the activity level parameter and control the activity level parameter in accordance with the particle therapy plan simultaneously, thereby further improving efficiency in using particle beams in the particle therapy.

The foregoing embodiments and modifications have been described using the particle therapy as an example of the radiotherapy. However, the radiotherapy in the present embodiment may be high-energy X-ray therapy. As a radiotherapy apparatus that emits high-energy X-ray, a LINAC (linear accelerator) may be used, for example.

Unlike particle beams, the ionization strength of X-rays peaks immediately upon entering the body of a patient, and reduces as the rays progress. In other words, X-rays are not suitable for spot irradiation. When an administered dose distribution is modified in the X-ray therapy, a method of changing an irradiation direction of X-rays is usually adopted. Hereinafter, an example where an irradiation direction of X-rays will be described. In the description hereinafter, suppose a strategy of irradiating only the active area with X-rays is adopted.

FIG. 11 is a diagram showing an example of the modification of the therapy plan relating to an X-ray therapy. As shown in FIG. 11, suppose the irradiation direction D3 is planned on Day 1 of the X-ray therapy. The tumor area TA of the X-ray irradiation target includes an active area TA1 and a non-active area TA2. While avoiding the temporal the non-active area TA2, the irradiation direction D3 is set so that the active area TA1 is irradiated with X-rays as much as possible, and only the shaded area is irradiated with X-rays. At this time, the irradiation area is determined with a margin added to the active area TA1 in consideration of patient's body motion and uncertainty of the therapy device.

As described above, the active area TA1 and the non-active area TA2 change with time. The irradiation direction D3 is changed in accordance with the locations of the active area TA1 and the non-active area TA2, so that the active area TA1 is irradiated with X-rays as much as possible while the non-active area. TA2 is avoided, and only the shaded area is irradiated with X-rays. For example, as shown in FIG. 11, on Day N of the radiotherapy, a dose is administered to the non-active area TA2 in the case of the radiation direction D3. Accordingly, an irradiation direction D4 for example is set so that the active area TA1 is irradiated with X-rays as much as possible while the non-active area TA2 is avoided, and only the shaded area is irradiated with X-rays. Thus, the present embodiment is applicable not only to particle therapy but also to radiotherapy. Although the example of one-direction irradiation is explained herein for the sake of simple description, multiple-direction irradiation is more effective in improving the delivery of a dose to the active area TA1 and reducing a dose delivered to the non-active area TA2.

According to at least one of the above-described embodiments, it is possible to improve efficiency in using radiation in radiotherapy.

The term "processor" used in the foregoing description means, circuitry, for example, a CPU, a GPU, an application specific integrated circuit (ASIC), or a programmable logic device (PLD). The PLD includes a simple programmable logic device (SPLD), a complex programmable logic device (CPLD), and a field programmable gate array (FPGA). The processor realizes its function by reading and executing the program stored in the storage circuitry. The storage circuitry storing the program thereon is a computer-readable non-transitory storage medium. Instead of storing a program on the storage circuitry, the program may be directly integrated into the circuitry of the processor. In this case, the function is activated by reading and executing the program integrated into the circuitry. The function corresponding to the program may be realized by a combination of logic circuits, and not by executing the program. Each processor of the present embodiment is not limited to a case where each processor is configured as a single circuit; a plurality of independent circuits may be combined into one processor to realize the function of the processor. Furthermore, a plurality of constituent elements shown in FIGS. 1 and 2 may be integrated into one processor to implement the functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A radiotherapy support apparatus, comprising:
processing circuitry configured to
obtain an activity level distribution representing radiation resistance in a tumor area of a subject, the activity level distribution being a distribution of at least one of perfusion information and metabolism information of the subject; and divide the tumor area into a plurality of areas in accordance with the radiation resistance represented by the activity level distribution, and set a radiation administered dose for each of the plurality of areas, in accordance with the radiation resistance of the corresponding area, to generate a first treatment plan.

2. The radiotherapy support apparatus according to claim 1, wherein the processing circuitry is further configured to obtain a second treatment plan that is produced in advance for the subject, and generate the first treatment plan by modifying the second treatment plan in accordance with the activity level distribution.

3. The radiotherapy support apparatus according to claim 2, wherein the processing circuitry is further configured to modify the radiation administered dose by modifying a distribution of spot irradiations to the tumor area in accordance with the activity level distribution.

4. The radiotherapy support apparatus according to claim 2, wherein the processing circuitry is further configured to modify the radiation administered dose by modifying an irradiation direction of radiation irradiated to the tumor area in accordance with the activity level distribution.

5. The radiotherapy support apparatus according to claim 2, wherein the processing circuitry is further configured to decrease the radiation administered dose for each of the plurality of areas as its radiation resistance becomes higher.

6. The radiotherapy support apparatus according to claim 2, wherein the processing circuitry is further configured to decrease the radiation administered dose for each of the plurality of areas as its radiation resistance becomes higher, and increase the radiation administered dose for each of the plurality of areas as its radiation resistance becomes lower.

7. The radiotherapy support apparatus according to claim 2, wherein the processing circuitry is further configured to increase the radiation administered dose for each of the plurality of areas as its radiation resistance becomes higher, and decrease the radiation administered dose for each of the plurality of areas as its radiation resistance becomes lower.

8. The radiotherapy support apparatus according to claim 2, wherein the processing circuitry is further configured to specify, as the plurality of areas, an active area where radiation resistance is low and a non-active area where radiation resistance is high.

9. The radiotherapy support apparatus according to claim 8, wherein the processing circuitry is further configured to:
re-specify an active area and a non-active area in the tumor area after a radiotherapy according to the second treatment plan, and
produce a third treatment plan in which an irradiation dose to the re-specified active area is higher than an irradiation dose to the re-specified non-active area.

10. The radiotherapy support apparatus according to claim 9, wherein the processing circuitry is further configured to cause a display to display a medical image used in the first treatment plan, and superimpose, on the medical image, a cumulative dose for irradiation.

11. The radiotherapy support apparatus according to claim 9, wherein the processing circuitry is further configured to cause a display to display a medical image used in the first treatment plan, multiply the active level distribution with the radiation distribution of each treatment session to generate treatment effectiveness distribution, and superimpose the treatment effectiveness distribution on the medical image.

12. The radiotherapy support apparatus according to claim 9, wherein the processing circuitry is further configured to cause a display to display a medical image used in the first treatment plan, multiply the active level distribution with the radiation distribution of each treatment session to generate treatment effectiveness distribution, correct the treatment effectiveness distribution with characteristics of an irradiation beam and sensitivity of each tissue, and superimpose the corrected treatment effectiveness distribution on the medical image.

13. The radiotherapy support apparatus according to claim 9, wherein the processing circuitry is further configured to produce, for the specified active area or in the re-specified active area, the first treatment plan so that a radiotherapy is repeated until a cumulative dose of irradiated radiation reaches a predetermined dose.

14. The radiotherapy support apparatus according to claim 1, wherein the activity level distribution is a distribution of the perfusion information in the tumor area.

15. The radiotherapy support apparatus according to claim 14, wherein the perfusion information includes information measured by a PET apparatus, a PET-CT apparatus, a SPECT apparatus, an X-ray CT apparatus, an ultrasonic diagnostic apparatus, or an MRI apparatus.

16. The radiotherapy support apparatus according to claim 1, wherein the activity level distribution is a distribution of the metabolism information in the tumor area.

17. The radiotherapy support apparatus according to claim 16, wherein the metabolism information includes information measured by a PET apparatus, a PET-CT apparatus, a SPECT apparatus, an X-ray CT apparatus, an ultrasonic diagnostic apparatus, or an MRI apparatus.

18. The radiotherapy support apparatus according to claim 1, wherein the processing circuitry is further configured to:
obtain a first activity level distribution of the tumor area and a second activity level distribution of normal tissue in the vicinity of the tumor area, and
normalize the first activity level distribution by using the second activity level distribution.

19. The radiotherapy support apparatus according to claim 1, wherein the processing circuitry is further configured to cause a display to display a medical image used in the first treatment plan, and superimpose the activity level distribution on the medical image.

20. The radiotherapy support apparatus according to claim 1, wherein the processing circuitry is further configured to produce the first treatment plan in which the radiation dose distribution of the tumor area changes in accordance with a temporal change of radiation resistance.

21. The radiotherapy support apparatus according to claim 20, wherein the processing circuitry is further configured to produce the first treatment plan in which a plurality of spread-out Bragg peaks are formed in a depth direction in the tumor area.

22. A radiotherapy system comprising a processor and an irradiation apparatus, wherein the processor is configured to:
obtain an activity level distribution representing radiation resistance in a tumor area of a subject, the activity level distribution being a distribution of at least one of perfusion information and metabolism information of the subject; and
divide the tumor area into a plurality of areas in accordance with the radiation resistance represented by the activity level distribution, and set a radiation administered dose for each of the plurality of areas, in accordance with the radiation resistance of the corresponding area, to generate a first treatment plan, and the irradiation apparatus irradiates the tumor area with radiation based on the first treatment plan.

* * * * *